US009212375B2

(12) United States Patent
Tobey et al.

(10) Patent No.: US 9,212,375 B2
(45) Date of Patent: Dec. 15, 2015

(54) METHOD FOR PRODUCING C2 OXYGENATES BY FERMENTATION USING HIGH OXIDATION STATE SULFUR

(75) Inventors: Richard E. Tobey, St. Charles, IL (US);
Toby D. Allen, Aurora, IL (US); Peter Martin Lokken, Chicago, IL (US);
Andrew James Heinen, Naperville, IL (US); Gengsheng Chen, Wilmette, IL (US)

(73) Assignee: COSKATA, LLC, Warrenville, IL (US)

( * ) Notice: Subject to any disclaimer, the term of this patent is extended or adjusted under 35 U.S.C. 154(b) by 243 days.

(21) Appl. No.: 13/546,703

(22) Filed: Jul. 11, 2012

(65) Prior Publication Data

US 2014/0017747 A1   Jan. 16, 2014

(51) Int. Cl.
C12P 7/54 (2006.01)
C12P 7/06 (2006.01)

(52) U.S. Cl.
CPC . *C12P 7/54* (2013.01); *C12P 7/065* (2013.01);
Y02E 50/17 (2013.01)

(58) Field of Classification Search
None
See application file for complete search history.

(56) References Cited

U.S. PATENT DOCUMENTS

| | | | |
|---|---|---|---|
| 2,474,139 A * | 6/1949 | Block | 435/105 |
| 5,173,429 A | 12/1992 | Gaddy et al. | |
| 5,593,886 A | 1/1997 | Gaddy | |
| 5,807,722 A | 9/1998 | Gaddy | |
| 5,821,111 A | 10/1998 | Grady et al. | |
| 6,136,577 A | 10/2000 | Gaddy | |
| 6,340,581 B1 | 1/2002 | Gaddy | |
| 7,285,402 B2 | 10/2007 | Gaddy et al. | |
| 2009/0215142 A1* | 8/2009 | Tsai et al. | 435/170 |
| 2011/0104770 A1* | 5/2011 | Tobey | 435/140 |
| 2011/0229947 A1* | 9/2011 | Zahn et al. | 435/161 |
| 2011/0300593 A1 | 12/2011 | Mihalcea | |

OTHER PUBLICATIONS

Hernandez-Eugenio, G. et al., *Clostridium thiosulfatireducens* sp. nov., a proteolytic, thiosulfate- and sulfur-reducing bacterium isolated from an upflow anaerobic sludge blanket (UASBB) reactor., International Journal of Systematic and Evolutionary Microbiology (2002), 52,1461-1468.
Mechichi, T., et al., *Clostridium peptidivorans* sp. nov., a peptide-fermenting bacterium from an olive mill wastewater treatment digester, International Journal of Systematic and Evolutionary Microbiology (2000), 50, 1259-1264.
Sallam, A., et al., *Clostridium sulfidigenes* sp. nov., a mesophilic, proteolytic, thiosulfate- and sulfur-reducing bacterium isolated from pond sediment. International Journal of Systematic and Evolutionary Microbiology (2009), 59, 1661-1665.

(Continued)

*Primary Examiner* — Alexander Kim

(57) ABSTRACT

The invention relates to improvements in the production of ethanol and acetate by microbial fermentation, particularly to production of alcohols by microbial fermentation of a substrate comprising CO and the addition of an inorganic sulfur additive. It more particularly relates to the provision of an inorganic organic sulfur source to a fermentation system such that one or more microorganisms convert a substrate comprising CO to ethanol. In one aspect the invention uses a sulfur additive comprising inorganic sulfur compounds having a +2 to a +4 sulfur oxidation state that produces sulfur oxoanions and hydrosulfur oxoanions in an aqueous fermentation medium.

27 Claims, 22 Drawing Sheets

(56) References Cited

OTHER PUBLICATIONS

Fazio, T., et al., A review of sulphites in foods: analytical methodology and reported findings, Food Additives and Contaminants, 1990, vol. 7, No. 4, 433-454.

Nieves I.U., et al., Effect of reduced sulfur compounds on the fermentation of phosphoric acid pretreated sugarcane bagasse by ethanologenic *Escherichia coli.*, Bioresource Technology 102 (2011), 5145-5152.

* cited by examiner

METHOD FOR PRODUCING C2 OXYGENATES BY FERMENTATION USING HIGH OXIDATION STATE SULFUR

FIELD OF THE INVENTION

This invention relates to method for the production of ethanol and/or acetate from substrates of carbon monoxide and/or carbon dioxide and hydrogen by anaerobic fermentation using carboxydotrophic microorganisms. More particularly, the invention pertains to using specific sources of inorganic sulfur to supply the biological sulfur needs of the microorganisms in a manner that is more cost effective and beneficial to such production of ethanol and acetate.

BACKGROUND

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. Since these feed sources compete with the human food supply much recent work has focused on alternative feed sources for biofuels and other chemicals.

One alternate source of feeds is lignocellulosic feedstocks such as forest residues, trees from plantations, straws, grasses and other agricultural residues. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose (C6 sugar polymers), hemicellulose (various C5 and C6 sugar polymers), and lignin (aromatic and ether linked hetero polymers). Then other well-known technologies can convert the lignocellulosic biomass feed to syngas (also known as synthesis gas, primarily a mix of CO, $H_2$ and $CO_2$ with other components such as $CH_4$, $N_2$, $NH_3$, $H_2S$ and other trace gases) This syngas is then fermented with anaerobic microorganisms to produce biofuels such as ethanol, n-butanol or chemicals such as acetic acid, butyric acid and the like. U.S. Pat. No. 7,285,402, the teachings of which are incorporated by reference herein, discloses methods for converting carbon monoxide, carbon dioxide, and hydrogen to acetic acid and ethanol by fermentation using anaerobic bacteria.

Anaerobic fermentations to produce biofuels and other chemicals can utilize any gaseous substrates that provide a carbon monoxide and/or carbon dioxide and hydrogen from a variety of sources. For example, US Patent Publication 2011/0300593 discloses sources such as steel mill off-gas as source of carbon monoxide and the teachings of which are incorporated by reference herein. Many other sources of substrates are available. For example, syngas can be made from many other carbonaceous feedstocks such as natural gas, reformed gas, peat, petroleum coke, coal, solid waste and land fill gas.

Ethanol can be produced from CO, $CO_2$ and $H_2$ using a variety of anaerobic bacteria, in particular such as those from the genus *Clostridium*. For example, various strains of bacteria that produce ethanol from gases are described and include *Clostridium ljungdahlii, Clostridium autoethanogenum* and *Clostridium coskatii* all of which are described further herein.

The production of ethanol and other products by the anaerobic microorganisms is influenced by many operating conditions within the fermentation zone. (see U.S. Pat. Nos. 5,173,429, 5,593,886, and 6,368,819, WO 98/00558 and WO 02/08438) Two primary conditions affecting the microorganism performance are the pH and oxidation-reduction potential (ORP) of the fermentation zone. WO2009/022925 discloses the effect of pH and ORP in the conversion of the gaseous substrates to products.

Microorganisms used in metabolic processes require nutrients and micronutrients and the particular supply of the nutrients can have profound effects on the growth and sustainability of the microorganisms. In fact these nutrients may be required to enable the microorganism to use carbon monoxide as its source of energy. For example, the microorganism may require the presence of metal co-factors for the metabolic functions of carbon monoxide dehydrogenase (CODH), and acetyl-CoA synthase (ACS). It is important that all of the required nutrients are provided in the proper amount and a bioavailable form.

Another of the required nutrients is a source of reduced sulfur, usually in the form of an organic sulfide such as cysteine. The cysteine provides a sulfur source necessary to support enzymatic processes occurring in a microbial culture. It is well known that microorganisms require sulfur in their enzymatic processes. In fact, the electron transfer mediator, ferredoxin, as well as Wood-Ljungdahl pathway enzymes acetyl-CoA synthase, and carbon monoxide dehydrogenase contain sulfur. Therefore, it is important to add sulfur in a bioavailable form and in sufficient supply to avoid inhibiting the growth or production of product by the microorganism.

As an alternative to cysteine, hydrogen sulfide has been found in many instances to be a source of the reduced sulfur needed for the metabolic processes of the microorganisms. Sulfur sources such as sulfide exist in equilibrium with hydrogen sulfide in typical fermentation media. Although hydrogen sulfide is less expensive than cysteine, it is toxic and thus requires special handling and is particularly dangerous in pure form. Supplying sulfur in the form of a sulfide salt such as sodium sulfide still results in a hydrogen sulfide concentration in the fermenter that may decrease over time due to evaporation. Moreover, hydrogen sulfide has a limited solubility in the media. Hydrogen sulfide may become highly volatile under the certain conditions that may be desired in the fermentation zone thereby exacerbating its use as a sulfur source. As a result, of the limited solubility of hydrogen sulfide in water the concentration of sulfur in solution can be significantly reduced by the conditions within fermentation medium. Accordingly, identification of improved or alternative sulfur sources for the microorganism in alcohol production required in fermentation systems using carbon monoxide or hydrogen and carbon dioxide gases as a feedstock would aid in achieving high alcohol production rates and low process operating costs.

Accordingly, the methods for producing ethanol or acetate from anaerobic fermentations would benefit from the discovery of sulfur compounds that can inexpensively provide the biological sulfur needs of the microorganisms under favorable fermentation conditions while also eliminating the disadvantages of hydrogen sulfide as a sulfur source.

US Patent Publication 20110300593 discloses the use of alternate sulfur sources. This document only specifically describes polysulfide, polysulfides, elemental sulfur and colloidal sulfur as the inorganic sulfur compounds for use as an alternative sulfur source. More importantly, the document describes the use of these specific sulfur compounds as means of providing hydrogen sulfide as the active species in the fermentation medium. As a result, this reference does not identify a sulfur additive that will provide a biologically available form of sulfur other than hydrogen sulfide and therefore does not overcome the high volatility problems of hydrogen sulfide.

Methods are sought to enhance the economics of syngas fermentation to produce C2 oxygenated organic compounds where the sulfur nutrient can be effectively and inexpensively supplied by the processes at an "as needed" rate.

SUMMARY OF THE INVENTION

This invention provides methods for the bioconversion of syngas to a C2 oxygenated organic compounds such as ethanol and acetate where the supply of the sulfur nutrient is provided by a sulfur additive that contributes sulfur oxyanions or hydrosulfur oxyanions to liquid nutrient medium in a form that meets the metabolic needs of the microorganism while facilitating operation of the fermentation zone at pH that will inhibit the growth of contaminating microorganisms. It was surprisingly discovered that such compounds can supply the nutritional sulfur needs of the carboxydotrophic microorganisms in the production of ethanol and acetate from substrates of CO, $CO_2$ and $H_2$. This class of compounds includes the bisulfites that are routinely used as antimicrobial agents in various food products. Ordinarily one would have expected such compounds to interfere with the growth and viability of microorganisms. Thus, it was surprising to discover that such compounds can be used beneficially in providing the sulfur species that will satisfy the metabolic requirements of the microorganisms while avoiding the volatility problems of hydrogen sulfide at lower pH conditions in the fermentation zone.

In a broad aspect this invention provides a method for the production of C2 oxygenates using ethanol producing carboxydotrophic microorganisms while supplying sulfur to the fermentation medium in a bioavailable and highly soluble form. Maintaining a pH below 5.3 and more preferably below 5.1 is highly beneficial in inhibiting the growth of contaminating microorganisms in the fermentation zone. Common contaminants that can alter or disrupt the fermentation process are microorganisms that produce butyrates and can reduce the selectivity of the process for more desired ethanol products.

In supplying the higher oxidation state sulfur the invention uses the microorganism as the means to reduce the oxidation state of the sulfur to the usable form. It is proposed that in this manner the microorganism produces the hydrosulfide ($HS^-$) that it assimilates within the cell where it is used. This reduces the presence $HS^-$ in the liquid nutrient medium and helps to minimize any equilibrium concentration of hydrogen sulfide that would contribute to hydrogen sulfide emissions from the fermentation.

In particular embodiments, this invention is a method for producing C2 oxygenates by anaerobic fermentation with an ethanol-producing carboxydotrophic microorganism. The method comprises providing a sulfur additive comprising an S(II) to S(IV) inorganic sulfur compound that produces sulfur anions containing oxygen and/or oxygen and hydrogen atoms in an aqueous fermentation medium, contacting a microbial culture of the microorganism with a substrate comprising carbon monoxide, maintaining the microbial culture in the fermentation medium containing the sulfur additive and having a pH of less than 5.3, and recovering one or more C2 oxygenates from the fermentation medium. In a further embodiment the sulfur additive comprises an S(III) to S(IV) inorganic sulfur compound.

In a particular embodiment, the sulfur additive is sulfurous acid, bisulfite, metabisulfite, dithionite, thiosulfate, or a combination thereof. In a preferred embodiment, the sulfur additive is sulfurous acid, bisulfite, metabisulfite or combination thereof. In other embodiments the sulfur additive may include sodium bisulfite, sodium metabisulfite.

In a particular embodiment, the sulfur additive is present in the fermentation medium at a concentration of at least 0.1, typically in a range of 0.1 to 10 and preferably in a range of 0.5 to 2 mmol sulfur per gram dry cell weight of microorganism.

In a particular embodiment, the contacting of the microorganisms with the sulfur additive takes place in the presence of an added organic sulfur source and the concentration of the organic sulfur in the fermentation medium is reduced over time. In a preferred embodiment, the concentration of the organic sulfur in the fermentation medium is less than 0.3 mmol organic sulfur per gram dry cell weight of microorganism, and more preferably less than 0.1 mmol organic sulfur per gram dry cell weight of microorganism.

In another aspect, the invention provides a method of eliminating cysteine as an amino acid and sulfur source for addition to the liquid nutrient media of the fermentation. In a particular embodiment of this invention, the concentration of cysteine in the fermentation medium may be significantly decreased and preferably decreased to a concentration of less than 0.3 mmol per gram dry cell weight of microorganism. In a particular embodiment, cysteine addition to the fermentation medium may be eliminated completely.

In another aspect of the invention, the pH of the fermentation medium is kept in a range of 4.3 to 5.1, and preferably below 4.9.

In another aspect of the invention, the method includes a chelating agent in the fermentation medium. In a preferred embodiment, the invention uses ethylenediaminetetraacetic acid, diethylenetriaminepentaaceteic acid, nitrilotriacetic acid, sodium citrate, and mixtures thereof as a chelating agent.

Generally, ethanol is the preferred metabolite for production by the microorganisms. In most cases the other metabolites will be produced together with acetate in the fermentation of the substrate. It has been found that the methods of the invention can improve the alcohol to acid product ratio. Product ratios in the range of ethanol to acetate of greater than 5:1 and greater than 10:1 have been found along with higher ratios of 20:1 or more favoring alcohol over acetate.

One application of the invention is in the case where an organic sulfur source such as cysteine is used in first vessel to grow the microbial culture and then the microbial culture is transferred to a second vessel. The first vessel may also contain the sulfur additive if desired. The contacting of the microbial culture from the first vessel with the substrate may then take place in the separate second vessel. The second vessel may maintain the fermentation with little or no cysteine. In particular embodiments of this invention, the second fermentation vessel will be a larger volume fermentation vessel as practiced in seed train operations to passage the microbial culture up to commercial scale volumes. Such transfers of the microbial culture can continue to a third fermentation zone and to additional fermentation zones of higher volume. In a preferred embodiment, the concentration of organic sulfur such as cysteine will decrease as the volume of the fermentation zone increases. In a further embodiment the addition of cysteine to the fermentation zone will only continue in fermentation zones having a volume of less than 40,000 liters and more preferably less than 4,000 liters.

Accordingly in another embodiment, the invention is a method for reducing cysteine in the production of ethanol or acetate by anaerobic fermentation. The method comprises contacting a microbial culture of a carboxydotrophic microorganism with a substrate comprising carbon monoxide and growing the microbial culture under anaerobic conditions in a first fermentation zone containing cysteine at a first concentration of cysteine to produce a cysteine grown microbial culture in a first fermentation zone. Some or all of the cysteine grown microbial culture is transferred to a second fermentation zone containing a sulfur additive comprising an inorganic sulfur compound having a +2 to a +4 oxidation state (S(II)-S(IV)) that produces anions in the second fermentation zone consisting of sulfur atoms combined with oxygen and/or hydrogen atoms. A substrate comprising (i) carbon monoxide, (ii) carbon dioxide and hydrogen, or (iii) mixtures of (i) and (ii) is added to the second fermentation zone to convert the substrate to C2 oxygenates. One or more C2 oxygenates are recovered from the second fermentation zone.

DEFINITIONS

Figure 1:
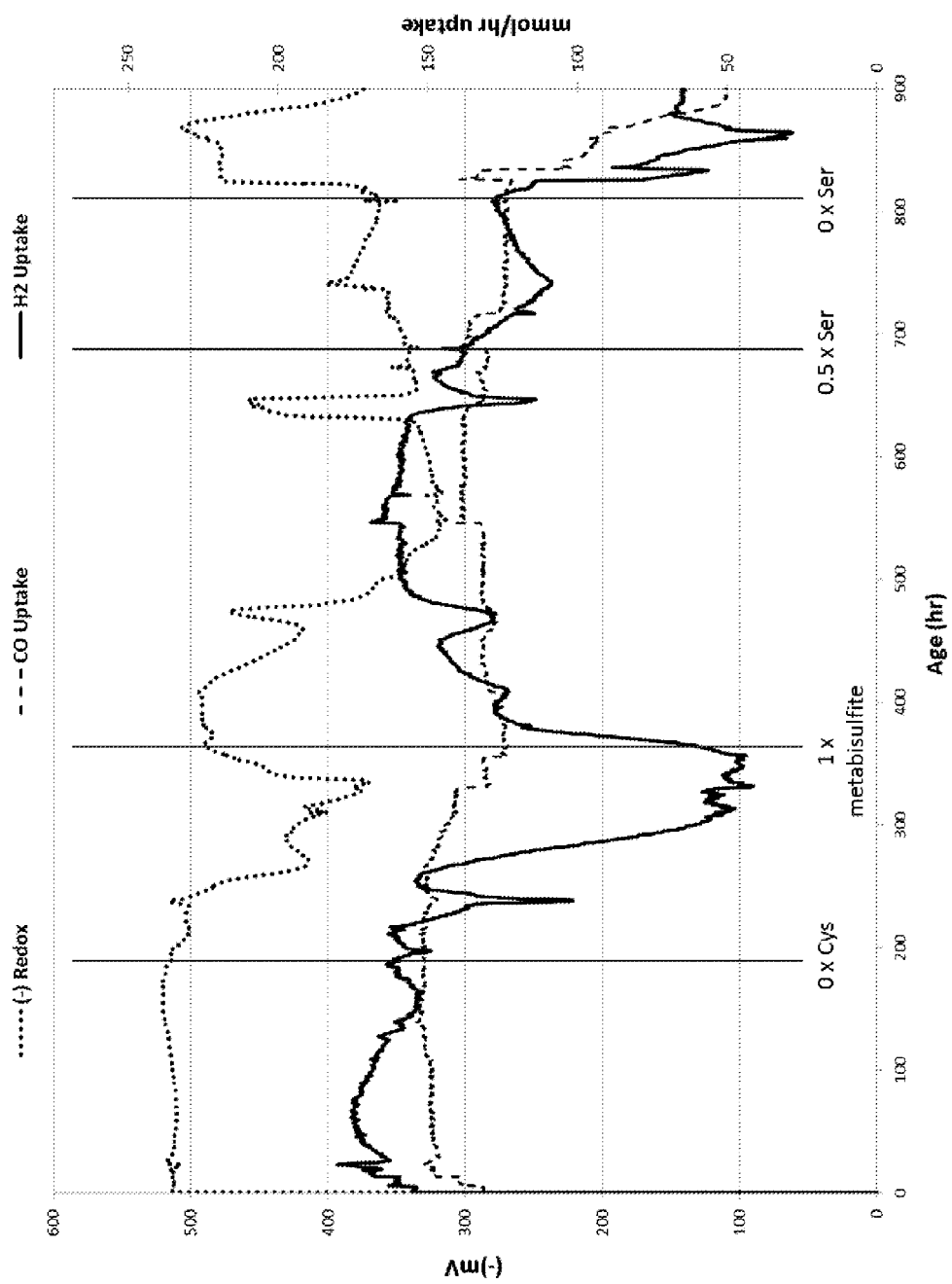
FIGS. 1 through 22 are plots of fermentation data showing gas uptake and product production from a series of continuation fermentation runs using the sulfur additive of this invention.

"Bioreactor" means any fermentation apparatus having at least one vessel for retaining microorganisms in the presence of a fermentation medium with the term vessel referring to any containment device including pipes, columns, membranes, screen and other like devices that can be arranged as continuous or batch reactors and may comprise a Bubble Column Bioreactor (BCBR), Continuous Stirred Tank Reactor (CSTR), an Immobilized Cell Reactor (ICR) such as a Membrane Supported Bioreactor (MSBR), jet loop reactors, trickle bed reactors, pipe reactors or any other device that provides the gas liquid contacting of the microorganisms with the substrate. The fermentation reactors used in this invention may be of any suitable design; however, preferably the design and operation provides for a high conversion of carbon monoxide and hydrogen to oxygenated organic compound.

"C2 oxygenate" means any molecule containing 2 carbon atoms, hydrogen atoms and at least one oxygen atom. Preferably, the C2 oxygenates will comprise ethanol, acetic acid and acetate anions.

"Microbial culture" means a mixture of microorganisms together with a liquid fermentation medium wherein the microorganisms are present in the form of a slurry, a suspension or fixed colonies. Microbial culture includes microorganisms suspended on moving support media such tubes rings or biochips or fixed on support media such as membranes or other porous or semi-porous media. The term microbial culture includes cultures made of a single strain of microorganism or multiple strains of microorganisms.

"Fermentation medium" means an aqueous liquid that contacts the microorganism and contains nutrients such as vitamins, minerals, amino acids, etc. that the microorganism needs for maintaining its biological functions as well as metabolic products produced by the microorganisms that are recovered from the fermentation medium. The fermentation medium may keep the microorganism suspended in planktonic state, may serve as a suspension medium to retain carrier material upon which the microorganisms are grown or may perfuse to and from the microbial culture across a support such as a membrane. The fermentation medium may directly receive the gaseous substrate and serve as the means for supplying the substrate to the microorganisms.

"Fermenting" or "fermentation" means any conversion of substrate by a microorganism whether the microorganism is in a phase of primary growth for the organism or in a phase of primarily producing metabolites as product.

"Mean cell retention time" means for continuous fermentation operations the total mass of the cells in the fermenter divided by the rate at which the biomass leaves the fermenter.

"Nutrient liquid" means an aqueous liquid that contains one or more of the nutrients such as vitamins, mineral, or amino acids needed by the microorganism to support or improve its biological functions and that is added to the fermentation medium or directly contacts a microbial culture.

"Organic sulfur" means any organosulfur compound defined as any sulfur derivative having at least one alkyl or aryl group.

The value of the term "redox potential" or "ORP" when quantified herein is taken as the measurement of such value with reference to an aqueous solution measured against Ag/Ag—Cl type electrode utilizing a 3.8M KCl electrolyte salt bridge.

"S(II)", "S(III)", and "S(IV)" mean a positive oxidation state of two, three, and four respectively of the sulfur atoms in a sulfur compound.

"Substrate(s)" means a gas or gases that provides the primary carbon and energy source to the microorganism and comprises at least one of carbon monoxide or a combination of carbon dioxide and hydrogen.

DETAILED DESCRIPTION OF THE INVENTION

This invention uses a unique class of inorganic sulfur compounds to provide the required sulfur to a fermentation process for the production of C2 oxygenates from the gaseous substrates that contain one or more of carbon monoxide and/or a combination of carbon dioxide and hydrogen. In most instances the primary advantage of the process is the elimination of the need for cysteine from the fermentation zone. In certain embodiments it may be possible to remove cysteine at the initiation of the fermentation or cysteine may be reduced and/or completely phased out as the fermentation progresses. This means the cysteine can be reduced to much lower levels than would be needed if cysteine were the primary source of bioavailable sulfur or may be eliminated from on-going fermentation operations not only as a sulfur source but also as a direct source of an amino acid. The inorganic sulfur additives of this invention have been found to provide sulfur in a highly sustainable form within the fermentation zone and to also enable the microorganism to thrive in both growth and production phases so that high titers of ethanol can be achieved from the fermentation section.

An essential component of this invention is the provision of a specific type of sulfur additive. The sulfur additive that may be used in this invention will comprise sulfur compounds having sulfur atoms present in a +2 to +4 oxidation state (S(II)-S(IV)). These additives can be any type of sulfur compounds that will provide sulfur oxoanions and/or hydrosulfur oxoanions. Particular anionic forms of the additive include sulfite, bisulfite, metabisulfite, sulfur dioxide, dithionite, and thiosulfate. The additive may be derived by the addition of various sulfur compounds such as sulfurous acid, sodium bisulfite, sodium metabisulfite, potassium metabisulfite, dithionous acid, sodium dithionite, sodium thiosulfate The sulfur additive once dispersed into the aqueous liquid of the fermentation medium will be present in its active anionic form. The oxoanions of sulfur and hydrosulfur oxoanions that are effective in this invention comprise the sulfite form $SO_3^{2-}$ and hydrogen sulfite (bisulfite) form $HSO_3^-$. While not wishing to be bound by any theory, the invention relies on the ability of the microorganisms to transport these sulfur oxoanions across the membrane of its cellular structure. Once inside the cell the microorganisms reduce the oxyanions to $HS^-$. The reaction sequence likely proceeds: $SO_3^{2-} \Rightarrow H_2S$ via sulfite reductase. Then, $HS^- + $O-acetylserine$\Rightarrow$cysteine via O-acetylserine sulfhydrylase. When exposed to water the sulfur compounds will dissociate into equilibrium mixtures of the sulfite anion and other positively charged species or neutral molecules. For example, using a sulfurous acid solution in water as an additive will result in an equilibrium of sulfur dioxide and the bisulfite ion according to the following formula:

$$H_2SO_3 + H_2O \rightleftharpoons HSO_3^- + H^+$$

With the disassociation constants—
$K_a = 1.38 \times 10^{-2}$; $pK_a = 1.86$.

Similarly, aqueous sulfur dioxide will bind with water and deprotonate according to the combined formula and pKa:

$$SO_2 + H_2O \rightleftharpoons HSO_3^- + H^+$$

with the disassociation constants—
$K_a = 1.54 \times 10^{-2}$; $pK_a = 1.81$.

The hydrogen sulfite will also exist in equilibrium with the sulfite ion according to the formula:

$$HSO_3^- \rightleftharpoons SO_3^{2-} + H^+$$

and is a weakly acidic species with a $pK_a$ of 6.97.

The dithionite anion ($[S_2O_4]^{2-}$), is another sulfur oxoanion that may be derived for use in this invention from dithionous acid and $H_2S_2O_4$ that will upon hydrolysis yield an equilibrium mixture of thiosulfate and bisulfite according to the formula:

$$2S_2O_4^{-2} + H_2O \rightarrow S_2O_3^{-2} + 2HSO_3^{-1}.$$

Suitable sulfur additives are available in a wide variety of forms that will provide the sulfur additive and the oxoanions of sulfur for assimilation by the microorganisms. Those skilled in the art will appreciate that suitable inorganic salts of sulfur may be used to supply the sulfur additive of this invention. The usual forms of the additives will comprise sodium bisulfite, sodium metabisulfite, sulfurous acid, potassium metabisulfite, potassium bisulfite, or any other cationic-oxoanionic-sulfur combination. It is highly beneficial that the sulfur compound is substantially soluble in the fermentation medium and is non-toxic to the microbial culture at the effective concentration of the sulfur additive at any point in the microbial culture.

The invention will maintain the sulfur additive at or above a predetermined level. The sulfur additive can be added in an amount to supply all or a portion of the sulfur needed to meet the biological needs of the microorganisms. The sulfur additive is typically supplied in an amount sufficient to provide enough individual atoms of sulfur to meet the biological needs of the microorganisms. For steady state fermentation conditions supplying all of the sulfur for the biological needs of the microorganism typically requires a sulfur addition rate of at least 0.25 mmols of the sulfur additive per gram dry cell weight of the microorganism for monoatomic sulfur ions with such rate adjusted for ions with multiple sulfur atoms. A preferred rate of sulfur addition is in the range of 0.67 to 2 mmols of sulfur per gram dry cell weight of microorganism.

The sulfur additive can comprise a variety of inorganic sulfur sources that may decompose and/or release into the bioavailable sulfur species of this invention at different rates depending on variables such as pH, temperature, pressure, etc. The supply of the sulfur additive may need to vary over time in accordance with the decomposition and disassociation rates of the particular sulfur additive that is in use. Such adjustments in the type and/or amount of sulfur additive supply may be necessary to support growth and/or productivity of the microbial culture. Therefore, the fermentation may benefit from increasing the desirable sulfur species by supplying greater amounts of the sulfur additive or varying the type of sulfur additive at different times in the various stages of the fermentation.

In particular embodiments, the one or more inorganic sulfur compound is a solution of bisulfite compound such as sodium bisulfite obtained in preferred form as 5 molar bisulfite solution and diluted to provide a stock solution at a preferred concentration from of about 1.2 mM. The concentration of bisulfite in solution will depend on various factors including pH and solubility.

In another embodiment, it has been discovered that carboxydotrophic microorganisms can survive in growth media that does not include any supplemental amino acids, including cysteine, and whose source of sulfur is sulfurous acid ($H_2SO_3$). The sulfur atoms of sulfurous acid and metabisulfite exist in the +4 oxidation state. It is known that metabisulfite, sulfurous acid, sulfite, sulfur dioxide, and bisulfite all exist in equilibrium in water. T. Fazio and C. R. Warner. 1990. A Review of Sulphites in Foods: analytical methodology and findings. Food Addit. Contam. 7:433-454.

In a particular form of this embodiment, a microbial culture may be initiated with cysteine as a sulfur additive and subsequently receive reduced concentrations of cysteine (along with proportional increases in the sulfur additive) while experiencing little sustained change in hydrogen uptake. Agitation and gas flow may be manipulated to control gas mass transfer where desired. Satisfactory results can be obtained even where the nutrient liquid is fully free of metabisulfite and cysteine for periods of over 800 hours and sulfurous acid is left as the only sulfur source supplied by the nutrient liquid for assimilation by the microorganisms. (Sulfate anions are present in the media, but the typical microorganisms for use in this invention do not utilize sulfate in either an assimilatory or dissimilatory fashion.) In some cases serine addition may be useful as well.

In some cases, excess addition of S(IV) compounds may result in reduced hydrogen uptake despite changes to $K_La$. This may result from the known action of S(IV) compounds as inhibitors of microbial growth. Therefore the invention may benefit from monitoring of the level of provided S(IV) such that enough is provided to avoid any adverse effect of providing too little bioavailable sulfur, while avoiding the toxicity effects of too much S(IV). Again, the addition of excessive sulfur can also lead to the microbial culture releasing high levels of hydrogen sulfide that is hazardous and expensive to remove.

The proposed method of assimilation of sulfurous acid to the cell begins with sulfite reductase. At the working culture pH range of 4.5-5.3, sulfurous acid will chemically deprotonate to mainly form $HSO_3^-$ as the two pKa's of the species are 7.2 and 1.9. This bisulfite would then be biologically converted to $H_2S$ via this enzyme, at which point it is believed to assimilate to cysteine via acetylserine coupling. While it is not known if the gene, O-acetylserine sulfhydrolase, for this reaction is present in genome of the carboxydotrophic organisms of this invention, it is known that the sulfite reductase gene is in the genome of carboxydotrophic organisms of this invention. In addition, the presence of hydrogen sulfide in the exhaust gas of the fermenter, while not in the feed to the fermenter of the nutrient liquid, combined with the ability of the microorganisms to live on this S(IV) indicate that the O-acetylserine sulfhydrolase gene is present.

Sulfur may be added to fermentation medium by any suitable means. In accordance with this invention the sulfur additive may be added in any manner that makes the desired sulfur species biologically available to the organism in predetermined amounts at selected times in the fermentation. Preferably, the additive is injected directly into the fermentation medium as part of nutrient liquid addition that supplies other nutrients to the microbial culture. Thus the sulfur additive can be added intermittently or continuously in mixtures and at a concentration that can vary over the time of the fermentation. The sulfur additive may be supplied to the microbial culture at different locations of the culture, For example, at multiple addition points in a bioreactor having a fermentation vessel that suspends the microorganisms in a planktonic state. Supply of the sulfur additive will usually follow inoculation of the bioreactor with microbial culture and will increase as the culture grows and the metabolic sulfur needs of the fermentation increase. Supply of the additive is usually regulated to maintain a predetermined concentration of one or more of the hydrosulfur or sulfur oxoanions that the microorganisms will assimilate in the bioreactor.

Any suitable method may be used for determining the concentration of the sulfur additive in solution. The supply of the sulfur additive may be regulated in response to the presence of sulfide in the off-gas from the fermentation zone. The fermentation will typically release sulfide to the head space or gas phase above the fermentation medium. This sulfide may originate from sulfide that formed in the fermentation medium and never entered the microorganism (extracellular sulfide) or from sulfide exhausted from the microorganism (intracellular sulfide). This invention advantageously minimizes any formation of extracellular sulfide and the presence and the release of sulfide is an indication of oversupply of the sulfur additive to the fermentation medium. Therefore, monitoring the concentration of sulfide in the off-gas provides a good indication of whether the sulfur is present in a sufficient or excessive amount relative to the biological needs of the microorganisms. A significant presence of sulfide in the off-gas, typically greater than 0.05 vol % indicates an excess supply of the sulfur additive. Typically a sulfide concentration of 0.01% to 0.025% in the off-gas indicates a satisfactory addition rate of the sulfur additive. The absence of sulfide in the off-gas may indicate a shortage in meeting the biological requirements of the microorganisms and could affect the productivity of the microorganisms over time.

Some embodiments of this invention may advantageously use cysteine in initiating a fermentation operation. Cysteine may be beneficial in the initial passaging up of the microbial culture in to larger volume fermentations. The relatively low volumes of fermentation medium used in the initial growth stages of fermentation still allow the cost effective use of cysteine as part of initially bringing a fermentation operation up to commercial volumes. For instance, the use of cysteine in first series of fermentation vessels that provide the initial passaging of the series of reactors will only involve volumes from a few liters to a few thousand liters and will not impose any substantial economic penalty to the use of some cysteine. The greatest advantages to this invention come with the discovery that cysteine may be substantially reduced or eliminated from commercial fermentation zones that have liquid volumes of one million liters or more and the use of cysteine as the primary sulfur source in such fermentations would require 100 kilograms or more of cysteine per day.

In other embodiments the fermentation of this invention may benefit from the addition of certain amino acids to the fermentation medium. In the case where cysteine is phased out of an initial fermentation it may be advantageous to add one or supplemental amino acids to the fermentation medium during the transition of the microbial culture from cysteine to the sulfur additives of this invention. Amino acids such as methionine and serine may be useful in this regard, in particular serine.

In addition to the sulfur, the liquid nutrient medium will include a broad range of minerals, trace metal components, and vitamins. Trace metals are part of the liquid nutrient medium and ordinarily will include one or more of manganese, zinc, molybdenum, selenium, tungsten, iron, cobalt and nickel. The composition of various nutrient media for anaerobic fermentation is well known and are described in U.S. Pat. Nos. 5,173,429 and 5,593,886. Typical compounds and final concentrations for the nutrients are given in Tables 1 to 3.

TABLE 1

Minerals

| Components | Concentration Range (g/L) |
|---|---|
| NaCl | 0.5 to 4.0 |
| $NH_4Cl$ | 1.25 to 5.0 |
| KCl | 0.125 to 0.5 |
| $KH_2PO_4$ | 0.125 to 0.5 |
| $MgSO_4 \cdot 7H_2O$ | 0.25 to 1.0 |
| $CaCl_2 \cdot 2H_2O$ | 0.05 to 0.2 |

TABLE 2

Trace Metals

| Components | Concentration (mg/L) |
|---|---|
| $MnSO_4 \cdot H_2O$ | 1.9 to 7.6 |
| $FeSO_4 \cdot 7H_2O$ | 18.3 to 73.2 |
| $CoCl_2 \cdot 6H_2O$ | 1.8 to 7.2 |
| $ZnSO_4 \cdot 7H_2O$ | 1.0 to 4.0 |
| $NiCl_2 \cdot 6H_2O$ | 0.4 to 1.6 |
| $Na_2SeO_4$ | 0.5 to 2.0 |
| $Na_2WO_4 \cdot 2H_2O$ | 0.6 to 2.4 |

TABLE 3

Vitamins

| Components | Concentration (mg/L) |
|---|---|
| Thiamine•HCl | 0.05 to 0.2 |
| Calcium Pantothenate | 0.05 to 0.2 |
| Nicotinic acid | 0.005 to 0.1 |
| Biotin | 0.01 to 0.1 |

Any or all of the nutrients may be blended into one or more nutrient liquids for addition to the microbial culture. Nutrient liquids are typically added to the fermentation medium that contacts the microorganisms. Various blends of the nutrient liquid containing different nutrients may be mixed in batch form and added to the fermentation medium on a continual or intermittent basis. In a preferred embodiment, the nutrient liquid be mixed just upstream of entering the fermentation medium by receiving serial addition of solutions containing nutrient components. The use of multiple nutrient liquid stream and/or serial addition of component solution may aid in avoiding precipitation of nutrient components.

The addition rates of the various nutrients into the microbial culture may be determined by any suitable method. Such methods include determining the average needs of the microbial culture at different stages of growth and productivity and calculating the additions rates of the various components at different points in time. Monitoring may also take place by various sampling means in which the levels of the different nutrient components are directly measured and additions rates set or adjusted in response to predetermined ranges for such nutrients. The sampling may take place by the use of probes or direct analysis of recovered samples. Methodologies for such analysis are well known in the art and include mass spectroscopy, inductively coupled plasma mass spectroscopy, high performance liquid chromatography, ion exchange chromatography, atomic absorption spectroscopy, and/or atomic absorption mass spectroscopy as examples.

The addition of the nutrients, in particular the trace metals, may result in the formation of metal precipitates in the fermentation medium. Overall or localized concentration of the metal in the fermentation medium may result in such precipitates or precipitates may form in the preparation of various nutrient liquid solutions. The elimination of cysteine as a nutrient additive can exacerbate the formation of these precipitates since the addition of cysteine provides a chelate to the nutrient liquid and to the fermentation media.

The formation of the metal precipitate may be avoided by the addition of a metal chelate to the nutrient liquid and/or the fermentation medium. Suitable metal chelates that may be incorporated into the nutrient and/or fermentation medium include ethylenediaminetetraacetic acid (EDTA), diethylenetriaminepentaacetic acid (DTPA), and nitrilotriacetic acid (NTA), and sodium citrate. The metal chelate may be added at any concentration that will avoid the formation of the precipitate. Desirable metal chelate concentrations will vary primarily with the metals concentration in the fermentation medium or the nutrient liquid, temperature of the liquid, and pH of the liquid. Typical concentrations of the metal chelate will be in a molar ratio range of chelate to total transition metals (as defined by IUPAC numbering as Group 3 to 12 of the Periodic Table) of from 0.1:1 to 5:1, preferably from 0.1 to 1.0 and more preferably in a range of from 0.2 to 0.5.

In some cases it is desirable to control the redox potential of the microbial culture. Such controls include altering the redox potential (ORP) of the microbial culture by altering the $K_L a$ mass transfer coefficient. At other times reducing agents may be added directly to the culture on a continuous or periodic basis by injection directly into the culture, a fermentation medium, or addition to the nutrient liquid. In particular the sulfites and bisulfites are reducing agents such that their addition will serve to lower the redox potential of the fermentation medium. The redox potential is typically controlled to a level of less than −200 mV and preferably in a range of from −300 mV to −500 mV and more preferably in a range of from −350 to −450 mV. Redox potential is readily measured by well-known means such as an ORP probe. It is also known that lowering of the ORP can promote preferential production of alcohols over acids by the reduction of the acids.

Suitable reducing agents, in particular metal reducing agents for lowering the ORP are well known to those skilled in the art. Suitable reducing agents include Cr(II) and Ti(IV)

Preferably, the pH is kept relatively constant while adjusting the ORP. A pH of 5.3 may provide a suitable operation. The preferred pH for the microbial culture is in a range of from 5.1 to 4.3. A pH of below 5.1 is more typically used. For a variety of reasons a pH of 4.9 or below has been found beneficial with a pH range of 4.3 to 4.9 being particularly preferred. Lowering the pH can also slow the growth of the desired ethanol producing organisms therefore the pH is usually kept at or above 4.3, but for suitable organisms a lower pH may be used. A lower pH inhibits the growth of invasive species of microorganisms such as butyrigens, which produce chemicals such as butanol and butyric acid. In addition, the lower pH range, preferably 4.9 or below facilitates the maintenance of a low ORP in the microbial culture.

Any source of carbon monoxide and/or carbon dioxide and hydrogen may serve as a substrate for the fermentation of this invention. Sources of high carbon monoxide gas include coke oven gas, industrial waste gases from petroleum refining or steel mill waste gas. The invention is particularly suited for substrates that comprise syngas. Syngas may be derived from various sources, including, but not limited to, gasification of carbonaceous feedstock such as biomass, landfill gas, coal, natural gas, and petroleum.

The source of the syngas is not critical to the broad aspects of this invention. The syngas should, however, be free of components in concentrations that would be unduly adverse to the microorganisms used in the fermentation such as, but not limited to, hydrogen cyanide, alkenes, and alkynes and that would be adverse if present in the sought oxygenated organic compound such as tars and aromatics where ethanol is the sought product. Often the syngas contains 25 to 70, say, 30 to 65, mole percent carbon monoxide; 0 to 70, say, 30 to 65, mole percent hydrogen; and 1 to 20, say 3 to 15, mole percent carbon dioxide excluding nitrogen, methane, and water vapor from the concentration calculations.

The syngas may undergo treatment to improve its suitability for use in the fermentation. Such treatment may include the removal of particulate matter. It may also be beneficial to remove contaminants that can pose toxicity problems for the microorganisms and inhibit their growth or increase their mortality. Removal of cyanide, tars and acetylene compounds is particularly beneficial.

Contacting of the syngas with the microorganisms may take place in any type of bioreactor. Such bioreactors may provide for continuous or batch fermentation of the substrate with the microorganisms. Multiple individual vessels can be provided in the arrangement of the bioreactor. The arrangement of vessels may include separate vessels with at least one for the growth phase of the microorganisms and at least another vessel for a production phase where the product metabolites are produced at a higher rate than for the bioreactors in the growth phase.

The syngas is provided in a manner to enhance mass transfer of hydrogen and carbon monoxide to the aqueous fermentation medium for bioconversion by microorganisms to C2 oxygenates such as ethanol or acetate. Preferably, the syngas is continuously supplied.

The conditions of fermentation, including the density of microorganisms, liquid nutrient composition, and syngas residence time, are preferably sufficient to achieve the sought conversion efficiency of hydrogen and carbon monoxide and will vary depending upon the design of the fermentation reactor and its operation. Typical fermentation conditions that will apply to bioreactors are well known. In planktonic-type fermentations that suspend the microorganisms in a liquid fermentation media these conditions will include pressure, temperature, gas flow rate, pH, ORP, agitation rate, media flow, and mean cell retention time for continuous fermentation operations.

Fermentation medium is maintained under fermentation conditions and the syngas is provided therein in a manner that maximizes its utilization. The pressure may be subatmospheric, atmospheric or super atmospheric, and is usually in the range of from about 90 to 1000 KPa absolute and in some instances higher pressures may be desirable for biofilm fermentation reactors. As most reactor designs, especially for commercial scale operations, provide for a significant height of aqueous menstruum for the fermentation, the pressure will vary within the fermentation reactor based upon the static head. Pressure conditions will affect the performance of the fermentation and optimization of such conditions depend, among other things, upon the specific microorganisms that are used, the composition of the substrate and the type of bioreactor. Higher pressure conditions can increase the rate of transfer of substrate to an aqueous phase which will decrease the retention time of the gas phase components in a given liquid volume to achieve a desired conversion of substrate. It has been reported in WO 02/08438 that increased ethanol productivities of 10 to 20 times as many grams per liter per day may be obtained by operating under higher pressure on the order of 2 to 5 atmospheres. However, decreased retention times and higher productivities must be balanced against the structural requirements for operating large fermentation vessel under high pressure. For this reason it may be most advantageous to operate large bioreactors at or close to atmospheric pressure. Higher pressures may be advantageously used in bioreactors that fix microorganisms on various supports and therefore have relatively lower containment volumes that make use of higher pressures practical.

CO partial pressure can also be a limiting condition in the fermentation and a condition that will have greater impact at higher operating pressures in the fermentation. The process needs sufficient substrate to ensure continued growth and productivity by the microorganisms, however when the partial pressure of CO becomes too high it can become toxic to the microorganisms and inhibit their growth and continued survival.

One or more carboxydotrophic microorganisms may be used in the fermentation to produce the sought oxygenated organic compound. In particular embodiments, the fermentation reaction is carried out by one of more strains of acetogenic bacteria.

Bioconversions of CO and $H_2/CO_2$ to ethanol and acetate are well known. For example, in a recent book concise description of biochemical pathways and energetics of such bioconversions have been summarized by A. Das and L. G. Ljungdahl, *Electron Transport System in Acetogens* and by H. L. Drake and K. Kusel, *Diverse Physiologic Potential of Acetogens*, appearing respectively as Chapters 14 and 13 of Biochemistry and Physiology of Anaerobic Bacteria, L. G. Ljungdahl eds, Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and n-butanol. *Clostridium ragsdalei* may be used, for example, to ferment syngas to ethanol.

Suitable microorganisms and growth conditions include the anaerobic bacteria *Butyribacterium methylotrophicum*, having the identifying characteristics of ATCC 33266 which can be adapted to and utilize CO enabling the production of n-butanol as well as butyric acid as taught in the references: "Evidence for Production of n-Butanol from Carbon Monoxide by *Butyribacterium methylotrophicum*," Journal of Fermentation and Bioengineering, vol. 72, 1991, p. 58-60; "Production of butanol and ethanol from synthesis gas via fermentation," FUEL, vol. 70, May 1991, p. 615-619. Other suitable microorganisms include: *Clostridium ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogenum*-sp. nov., An anaerobic bacterium that produces ethanol from carbon monoxide, Jamal Abrini, Henry Naveau, Edomond-Jacques Nyns, Arch Microbiol., 1994, 345-351, Archives of Microbiology 1994, 161: 345-351; and *Clostridium coskatii* having the identifying characteristics of ATCC No. PTA-10522 and issued as U.S. Pat. No. 8,143,037. All of these references are incorporated herein in their entirety.

Suitable microorganisms for bioconversion of syngas to C2 oxygenates such as ethanol and acetate in accordance with this invention live and grow under anaerobic conditions, meaning that dissolved oxygen is essentially absent from the fermentation zone. Where large quantities of nutrient liquid or fermentation medium make-up are added to the microbial culture, such as continuous fermentations operating with a low mean cell retention time, the fermentation may benefit from the addition of one or more reducing agents to maintain anaerobic conditions and the ORP in a predetermined range.

Other additives to the fermentation medium may comprise buffering agents, trace metals, vitamins, minerals, salts, etc. Adjustments in the fermentation medium may create different conditions at different times such as growth and non-growth conditions which will affect the productivity of the microorganisms. U.S. Pat. No. 7,704,723, hereby incorporated by reference in its entirety, discloses the conditions and contents of suitable fermentation medium for bioconversion CO and $H_2/CO_2$ using anaerobic microorganisms.

Anaerobic fermentation conditions include a suitable temperature, say, between 25° and 60° C., frequently in the range of about 30° to 40° C. Highly preferred temperature conditions for this fermentation include temperatures in the range of 36° to 38° C.

The fermentation may be carried out in any of the bioreactors as previously described. Preferred reactors are those that can provide a high productivity of C2 oxygenates under industrially practical conditions. Bubble column bioreactors are favored for their ability to conserve energy requirements for the circulation and mixing of the substrate in the liquid phase. Membrane supported bioreactors can provide significant advantages in commercial operations by facilitating operations at higher pressure and reducing the water requirements for the fermentation.

Product recovery typically takes place by separating desired products from the fermentation medium. Any type of product recovery that recovers the desired products from the microbial culture can be used. In most cases the products are recovered from the fermentation medium which captures the metabolites from the microorganisms by intimate contact therewith. Usually a portion of the fermentation medium is withdrawn from time to time or continuously from the bioreactor for such product recovery. In the case of fermentation that suspends the microorganisms in a planktonic state or on a carrier material the withdrawal of the fermentation medium is typically made at a point at the upper portion of the liquid surface in the vessel. For bioreactor arrangements that fix the microorganisms to a solid support, such as membrane supported bioreactors or trickle bed bioreactors, the fermentation medium comprises a circulating fluid of which a portion is withdrawn.

Product recovery from the fermentation medium can consist of any known equipment arrangements for removal of residual cell material, separation and recovery of liquid products from the fermentation liquid, return of recovered fermentation liquid and purging of waste streams and materials. Either ethanol or acetate may be recovered from the fermentation liquid by methods that are well-known in the art. Suitable equipment arrangement can include filters, distillation columns, membrane systems and other separation equipment. US 2009/0215139 A1 shows an arrangement for a product recovery reactor that recovers an ethanol product from a bioreactor, herein incorporated by reference in its entirety. Distillation methods for the recovery of ethanol from fermentation medium results in an ethanol containing stream having an azeotropic mixture of ethanol and water (i.e., 95% ethanol and 5% water). Where an anhydrous ethanol product is desired the ethanol containing stream may undergo further purification by methods well-known in the art such as molecular sieve ethanol dehydration technology.

The fermentation will usually result in an incomplete utilization of the substrate. As a result, it has been found useful to recover substrate components from the bioreactor off-gas or from the fermentation medium. In particular carbon dioxide may be removed from the bioreactor or from the off-gas from a bioreactor. Any suitable carbon dioxide removal process may be used including amine extraction, alkaline salt extractions, water absorption, membrane separation, adsorptions/desorption, and physical absorption in organic solvents. In preferred aspects of the invention, the off-gas after carbon dioxide removal will contain at least about 15, say, between 15 and 50, mole percent of total hydrogen and carbon monoxide. Preferably, the carbon dioxide concentration in the off-gas after carbon dioxide removal is between about 2 and 40, more preferably between about 5 or 10 and 20, mole percent. The off-gas after carbon dioxide removal may contain at least about 5, and often about 10 to 20, mole percent nitrogen.

A preferred process for removal of carbon dioxide from gases is by contacting the gas with an aqueous solution containing oxygenated organic compounds. This process for removing carbon dioxide from gas to be fed to a reactor, including between sequential fermentation stages, is disclosed in U.S. Patent Publication No. 2008/0305539, filed Jul. 23, 2007, herein incorporated by reference in its entirety. See also, U.S. patent application Ser. No. 12/826,991, filed Jun. 30, 2010, herein incorporated by reference in its entirety, which discloses contacting a gas stream with a mixture of water and a surface active agent under pressure to sorb carbon dioxide and phase separating the gas and liquid stream to provide a gas stream with reduced carbon dioxide concentration to be used as feed to a reactor. U.S. Patent Publication No. 2008/0305539 A1 discloses the use of membranes to remove carbon dioxide from a membrane supported fermentation system to prevent dilution of concentrations of carbon monoxide and hydrogen in a multistage system. If desired, a portion of the carbon dioxide dissolved in the liquid phase of the fermentation medium can be removed. Any convenient unit operation for carbon dioxide removal can be used, but the preferred operation is separation by reducing the pressure to atmospheric or lower pressure to flash carbon dioxide gas from the liquid phase.

EXAMPLES

General Procedures

A series of continuous fermentation experiments were conducted to show the ability of various strains of microorganism to produce ethanol and acetate products in anaerobic fermentations using the sulfur additive of this invention. The experiments were conducted using a starting stock fermentation medium having nutrients in the ranges as given by tables 4-6. This media culture served as the base liquid media for the experiments.

TABLE 4

Mineral

| Components | Concentration (g/L) |
|---|---|
| $NH_4Cl$ | 2.5 |
| KCl | 0.25 |
| $KH_2PO_4$ | 0.5 |
| $MgSO_4 \cdot 7H_2O$ | 0.125 |
| $CaCl_2 \cdot 2H_2O$ | 0.05 |

TABLE 5

Trace metal

| Components | Concentration (mg/L) |
|---|---|
| $MnSO_4 \cdot H_2O$ | 3.8 to 7.5 |
| $FeSO_4 \cdot 7H_2O$ | 37 to 183 |
| $CoCl_2 \cdot 6H_2O$ | 3.6 to 7.2 |
| $ZnSO_4 \cdot 7H_2O$ | 2.0 to 9.8 |
| $NiCl_2 \cdot 6H_2O$ | 0.8 to 1.6 |
| $Na_2SeO_4$ | 1.0 to 2.0 |
| $Na_2WO_4$ | 0.6 to 1.2 |

TABLE 6

Vitamin

| Components | Concentration (mg/L) |
|---|---|
| Thiamine·HCl | 0.1 to 0.2 |
| Calcium Pantothenate | 0.1 to 0.3 |
| Nicotinic acid | 0.005 to 0.0015 |
| Biotin | 0.05 to 0.1 |

Quantities of the base liquid media described above were prepared by introducing 10 liters of water into 10 liter media feed carboys and adding the chemical components, with the exception of iron compounds, into the base liquid media in quantities that would provide the listed nutrients within the ranges set forth above. The media feed carboys were sparged for at least one day with nitrogen gas prior to addition of iron compounds and any other compounds to remove dissolved oxygen.

The procedures to establish the fermentation runs in the different experiments were conducted in the same manner unless otherwise noted. The standard procedure for the experiments started with the introduction of a "seed" culture in a seed vessel comprising a Biostat B supplied by Sartorius Stedim Biotech, Germany. An inoculum was added to either 4.5 L or 9 L of the liquid media in the seed vessel, depending on seed vessel volume. Fermentation continued in the seed vessel until an optical density (OD) of at least 1.5. All measurements of OD were measured by a spectrophotometer at a wavelength of 600 nm. After achieving the OD of 1.5 in the seed vessel, 1 L of microbial culture from the seed vessel was added, via an inoculation header driven by a Masterflex peristaltic pump, to a 10 liter fermentor containing 9 L of the liquid media described above. Unless otherwise noted, all continuous fermentation runs were conducted using 10-L Biostat C-DCU model fermenters obtained from Sartorius Stedim Biotech, Germany. Gas flow and agitation profiles, manual changes, or a combination of the two were employed to maintain healthy and active microbial cultures, as measured by gas uptake, OD and product profiles. Mean cell retention time (MCRT) was adjusted daily to reflect the equation MCRT=15/OD. Liquid media from the carboy was filter sterilized upon addition to the fermenter. All of the fermentations in the 10-L fermenters were at a super-atmospheric pressure and the pressure values represent gauge pressures unless otherwise noted. The off-gas from the fermenter was continually monitored using a mass spectrometer to measure the uptake of CO and hydrogen. Concentrations of product metabolites in the fermenter were analyzed by gas chromatography equipped with a flame ionization detector.

Example 1

A seed culture comprising *Clostridium coskatii* obtained from cryogenic stocks of the microorganism on deposit as ATCC No. PTA-10522 and described in U.S. Pat. No. 8,143,037 as described in US Patent was grown in a seed vessel and then introduced into the fermentor at the beginning of the continuous fermentation run according to the General Procedures as previously described herein. At the initiation of the run (hour 0) the base liquid media entering the fermenter contained cysteine at a concentration of 0.6 mM which provided cysteine in an amount equal to about 0.5× the typical base reference concentration for the molar addition of cysteine as the sole sulfur source to the fermenter. In addition, 1.2 mM of metabisulfite (average 0.2 mM/day/OD) was added to the liquid media to provide a 2× addition of sulfur atoms along with 1.2 mM of serine to provide 1× addition of an amino acid constituent. DTPA was used as a chelant in this run at a concentration of 0.79 g/L. Throughout the run gas flow remained relatively constant and ranged from about 100 to 300 ml/min and had a volumetric composition of 34% CO, 8% $CO_2$, 43% $H_2$ and 13% $CH_4$. Base liquid media addition was varied within a range of about 1.6 to 3.0 liters per day. Pressure throughout the run was maintained at 910 mbar and temperature throughout the run remained at approximately 37° C. At hour 185 of the run a base liquid media that no longer contained cysteine was supplied from the 10 L carboy. At hour 688 the serine concentration was dropped to 0.5× and then eventually to 0 at hour 808. The pH in the fermenter was initially maintained at value of about 5.3 and was allowed to fall starting at hour 185 until it reached a value of about 4.5 around hour 288. It was brought back up to 4.8 at about hour 330 and ranged between 4.8 and 4.5 through about hour 800.

FIG. 1 shows the operational values for the phase of the run starting from hour 0 through 900 hours. Agitation varied from about 290 to 475 rpm for providing some adjustment of the $K_L a$ to improve stabilization of the gas uptake. FIG. 1 shows a relatively stable uptake of CO through this phase of the run and that good utilization of the CO continued in the absence of cysteine. The run phase also showed overall good utilization of the hydrogen by its high uptake over most hours of the fermentation. Once serine was completely removed at 808 hours the remaining phases of the run showed a decline of the CO and hydrogen uptake. Colorimetric analysis of the off-gas also showed from 0 to 1350 ppm sulfide. After hour 808 the run became unstable and the run was terminated after unsuccessful attempts to stabilize it.

Figure 2:
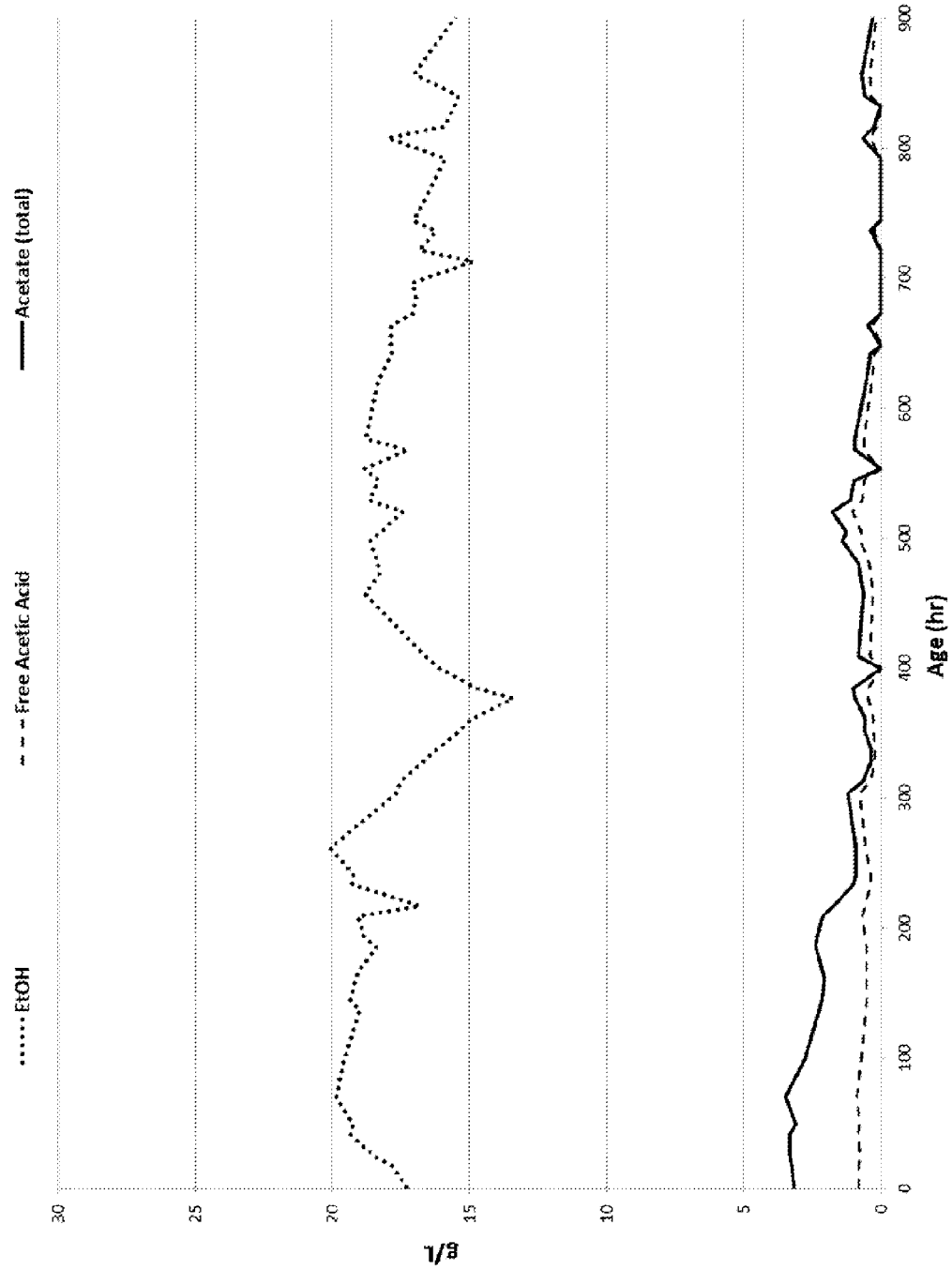

FIG. 2 shows a plot of the recovery of products for the 0 to 900 hour run phase. Overall the results of the product analysis show a high concentration of ethanol in the fermenter throughout the run phase despite the elimination of cysteine from the liquid media feed. The product data also shows a relatively low productivity of free acetic acid and total acetate. Throughout the run phase butanol and butyrate production were below detection limit of the gas chromatograph (~0.1 g/l).

Example 2

A seed culture comprising *Clostridium coskatii* obtained from the same cryostock as described in Example 1 was introduced into the fermentor at the beginning of the continuous fermentation run. At the initiation of the run the liquid media entering the fermenter contained cysteine at a concentration of 0.96 mM which provided a 0.8× normalized molar addition of sulfur to the fermenter (~0.064 mM/day/OD). Gas flow to the run started at about 100 ml/min, was increased step wise until reaching a value of about 200 ml/min at about hour 200 and remained at about 190 to 200 ml/min for the rest of the run. The gas had a volume percent composition of 34% CO, 10% $CO_2$, 43% $H_2$ and 12% $CH_4$.

Base liquid media addition was varied within a range of about 1.7 to 2.9 liters per day. DTPA was used as a chelant in this run at a concentration of 0.79 g/L. Pressure throughout the run was maintained at 910 mbar and temperature throughout the run remained at approximately 37° C. The pH of the fermentation medium was at approximately 5.3 throughout the run. After about 250 hours thiosulfate was added to the liquid media at a concentration of 1.9 mM to provide a 1.6× addition of thiosulfate as a bioavailable sulfur addition. In addition, the liquid media was also amended at the same time with 1.2 mM (~0.8 mM/day/OD) of L-serine to provide 1× of an amino acid constituent and L-methionine at a concentration of 0.02 mM/day/OD to provide 0.25× of another amino acid constituent. These conditions were established prior to the removal of cysteine at about hour 260 to acclimate the cultures to the new sulfur source. The run continued for about 200 hours with a decrease in hydrogen consumption. Cysteine was introduced again at about hour 457 at 0.6 mM for a 0.5× concentration (0.48 mM/day/OD) and thiosulfate addition was stopped. Hydrogen consumption continued to decrease until reaching a value of about 18 mmol/hr at about hour 540 and then rapidly rose again to about 160 mmol/hr at about hour 600. CO uptake reached a maximum value of about 200 mmol/hr at about hour 260 and then decreased to a range of about 170 to 140 mmol/hr for the remainder of the run.

The metabolite products in the fermentation medium were analyzed. The ethanol concentration increased in a generally linear manner until reaching a peak concentration of between 16 to 18 grams/liter from between hours 250 to 430 and subsequently dropped to about 11 gram/liter at about hour 575. Total acetate stayed at concentrations between 6 to 8 grams/liter from about hours 90 to 275 before dropping below 2 gram/liter from about hour 390 and for the rest of the run. The product data also shows a relatively low productivity of free acetic acid, below 2 grams/liter over the course of the run. Throughout the fermentation run butanol and butyrate production were below detection limit of the gas chromatograph (~0.1 g/l). Colorimetric analysis of the off-gas also showed sulfide at a concentration ranging from 20 to 360 ppm.

Example 3

A new run was established by carrying over a batch of the culture from the end of the run described in Example 2 and initiating a new run for this example. At the initiation of this run (hour 0) the base liquid media entering the fermenter contained cysteine at a concentration of 0.6 mM (~0.03 mM/day/OD) which provided 0.5× the typical base reference concentration for the standard molar addition of cysteine. In addition, 2.4 mM of metabisulfite was added to the liquid media at the initiation of the run to provide a 4× addition of sulfur atoms. Also at the initiation of the run L-methionine was added to the base liquid media at a concentration of 0.30 mM to provide a 0.25× addition of a sulfur bearing amino acid and serine was added to the base media at an average concentration of 1.2 mM (~0.066 mM/day/OD) to provide a 1× addition of non-sulfur bearing amino acid. Diethylenetriaminepentaacetic acid A chelant of DTPA was used in this run at concentration of 0.079 g/L. Addition of cysteine and methionine to the base liquid stopped at about hour 185. At about hour 360 metabisulfite addition to the base liquid was changed to 1.2 mM to provide a 2× addition of sulfur. Starting at about hour 670 sulfurous acid was added to the base liquid media at a concentration of 0.6 mM (~0.04 mM/day/OD) to provide a 0.5× addition of sulfur through sulfurous acid and metabisulfite addition was decreased from 1.2 mM to 0.6 mM to provide a 1× addition of sulfur from metabisulfite. The addition of metabisulfite to the base liquid stopped at about hour 800 at which time the addition of sulfurous acid was increased to 1.2 mM to provide a 1× addition of sulfur through sulfurous acid. The addition of sulfurous acid was lowered to an average of 0.6 mM (~0.04 mM/day/OD) at hour 1000 to provide a 0.5× total sulfur addition. Throughout the run gas flow remained relatively constant at 180 ml/min until hour 1080 when it was adjusted down to a low of about 130 and up to a high of about 260 ml/min to improve the stability of the run. The gas had a volumetric composition of 34% CO, 8% $CO_2$, 44% $H_2$ and 13% $CH_4$. After establishment of the run base liquid media addition was varied within a range of about 2.5 to 3.3 liter per day. Pressure was maintained at 910 mbar throughout the run and temperature throughout the run remained at approximately 37° C. The pH in the fermenter was initially maintained at value of about 5.3 until about hour 1080 and thereafter was maintained in a range of 4.8 to 4.9

Figure 3:
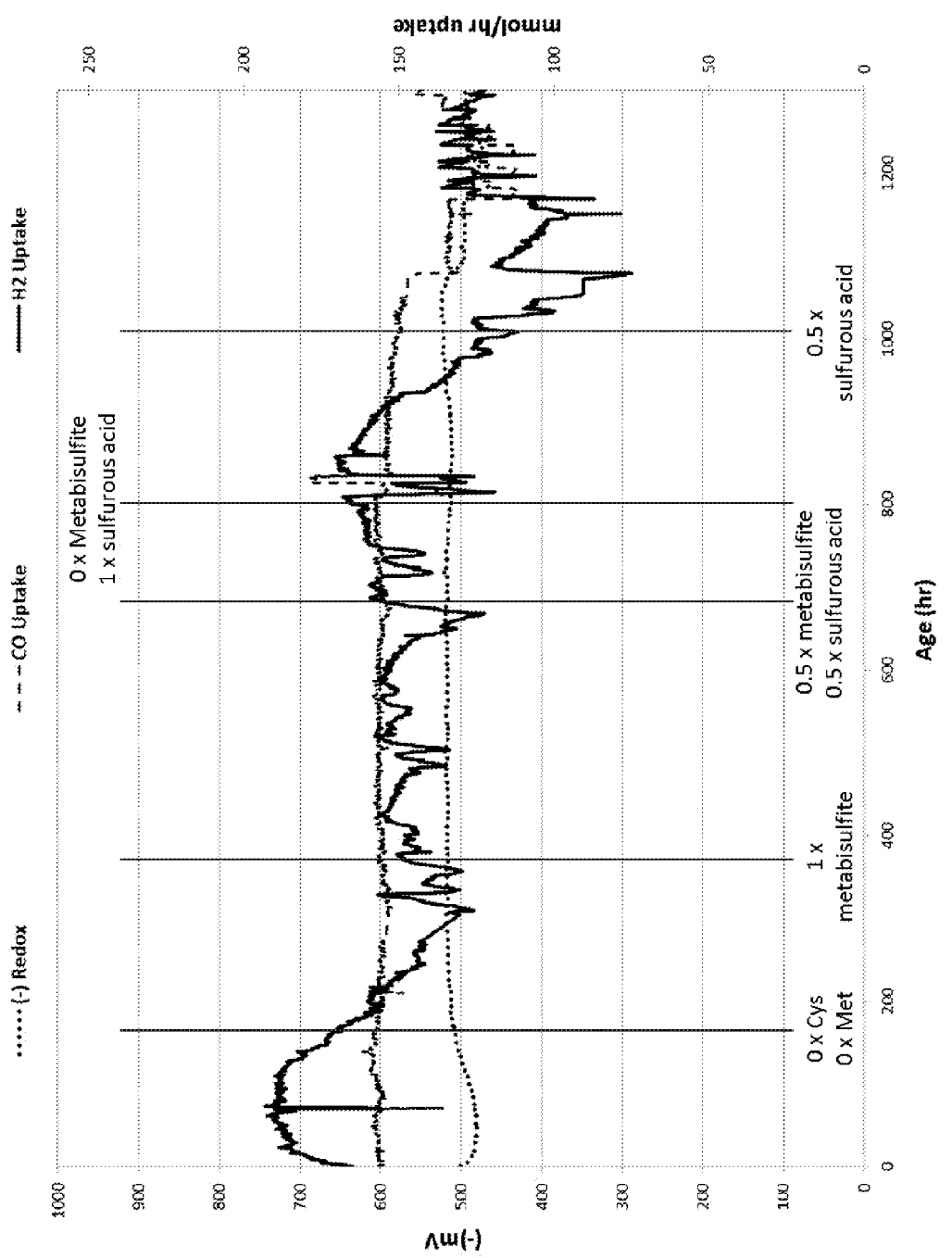

FIG. 3 shows the operational values for the phase of the run starting from hour 0 through 1300 hours. Agitation was kept in a narrow range of from 405 to 480 rpm over most of the phase of the run. FIG. 3 shows a very stable uptake of CO through this phase of the run and that good utilization of the CO continued in the absence of cysteine or any other amino acid. The run phase also showed overall good utilization of the hydrogen by its high uptake over most hours of the fermentation. Hydrogen uptake also remained relatively stable until hour 900 when it to decline and eventually became unstable. Colorimetric analysis of the off-gas also showed sulfide present throughout most of the run at a concentration ranging from 60 to 2600 ppm.

Figure 4:
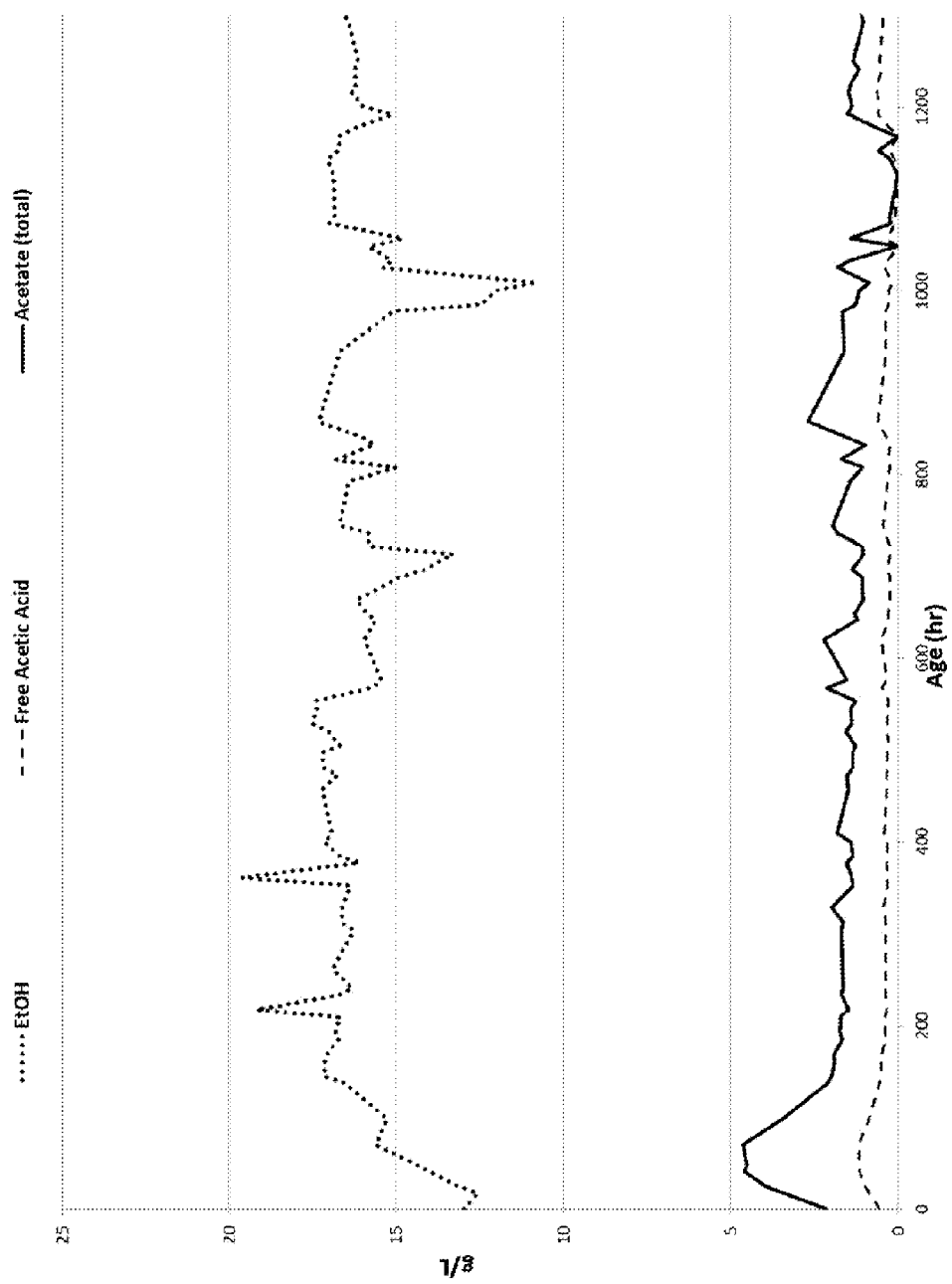

FIG. 4 shows a plot of the recovery of products for the 0 to 1300 hour run phase. Concentrations of product metabolites in the fermenter were analyzed by the same methods previously described. Overall the results of the product analysis show a high titer of ethanol in the fermenter throughout the run with the addition of metabisulfite or sulfurous acid phase despite the elimination of cysteine. After the run stabilized, FIG. 4 shows a relatively low production of acetic acid and total acetate for the majority of the run. Throughout the run phase butanol and butyrate production were below the detection limit of the gas chromatograph (~0.1 g/l).

Example 4

A seed culture comprising *Clostridium coskatii* obtained from the same cryostock as described in Example 1 was grown in a seed vessel and then introduced into the fermentor at the beginning of the continuous fermentation run according to the General Procedures as previously described herein. At the initiation of the run (hour 0) the base liquid media entering the fermenter contained serine at an average concentration of 1.2 mM (~0.14 mM/day/OD) to provide 1× of an amino acid constituent. In addition, an average of 0.6 mM (~0.06 mM/day/OD) of metabisulfite was added to the liquid media to provide a 1× addition of sulfur atoms and the seed culture was grown on metabisulfite without the addition of cysteine. DTPA was used as a chelant in this run at a concentration of 0.79 g/L. Gas flow was brought up over about the first 120 hours to a rate of about 140 ml/min and kept in the range of 140 to 200 ml/min for the first 500 hours and then increased to a rate of about 300 ml/min for the remaining phase of the run. The gas had a volumetric composition of 34% CO, 8% $CO_2$, 44% $H_2$ and 13% $CH_4$. Base liquid media addition was varied within a range of about 1 to 3.6 liter per day. Pressure was increased over the first 100 hours and then maintained at 930 mbar gauge throughout the run phase and temperature remained at approximately 37° C. At hour 337 the serine addition rate was dropped to 0.6 mM for a 0.5× addition and then to 0 at about hour 500. At hour 337 the rate of metabisulfite addition was decreased to an average of 0.3 mM (0.04 mM/day/OD) to provide a 0.5× addition rate of sulfur atoms. At about hour 650 the rate of metabisulfite addition was increased to an average of 0.5 mM to provide a 0.8× addition rate of sulfur atoms. The pH in the fermenter was maintained at value of about 4.8 throughout this phase of the run.

Figure 5:
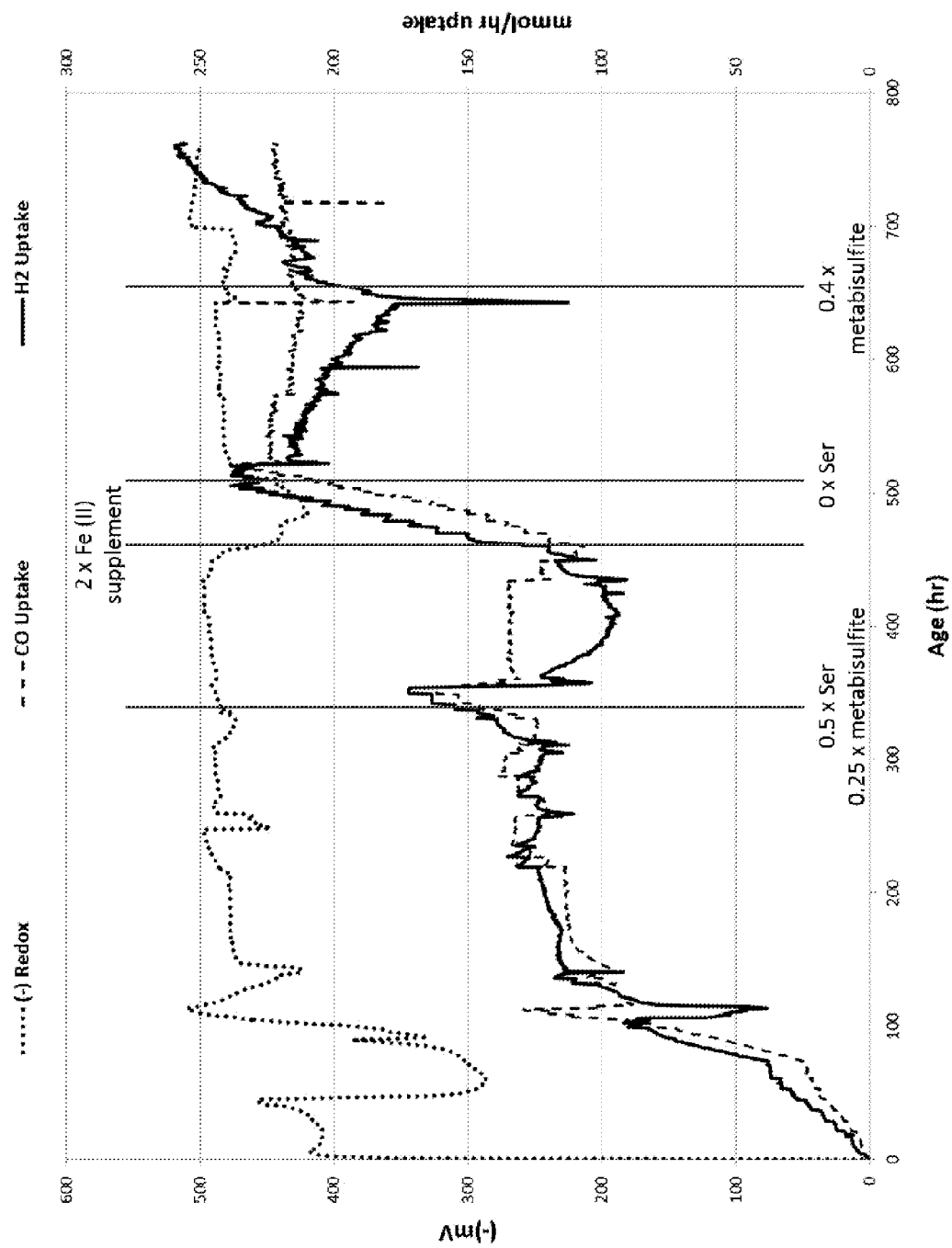

FIG. 5 shows the operational values for the phase of the run starting from hour 0 through 760 hours. After initial ramp-up, the agitation for the run remained relatively constant at a 400 rpm. FIG. 5 shows a relatively stable uptake of CO through this phase of the run with a first CO uptake rate at a gas flow rate in the range of 140 to 200 mL/min and an increased CO uptake rate again after 500 hours when the gas flow rate was held steady at 300 mL/min. Hydrogen uptake also remained relatively steady at first at lower values and then higher at higher values that coincided with the changes in the gas flow rate. Thus good utilization of the CO and hydrogen was found in the complete absence of cysteine addition to the liquid media. Colorimetric analysis of the off-gas also showed sulfide concentrations between 0 and 600 ppm in the effluent gas stream.

Figure 6:
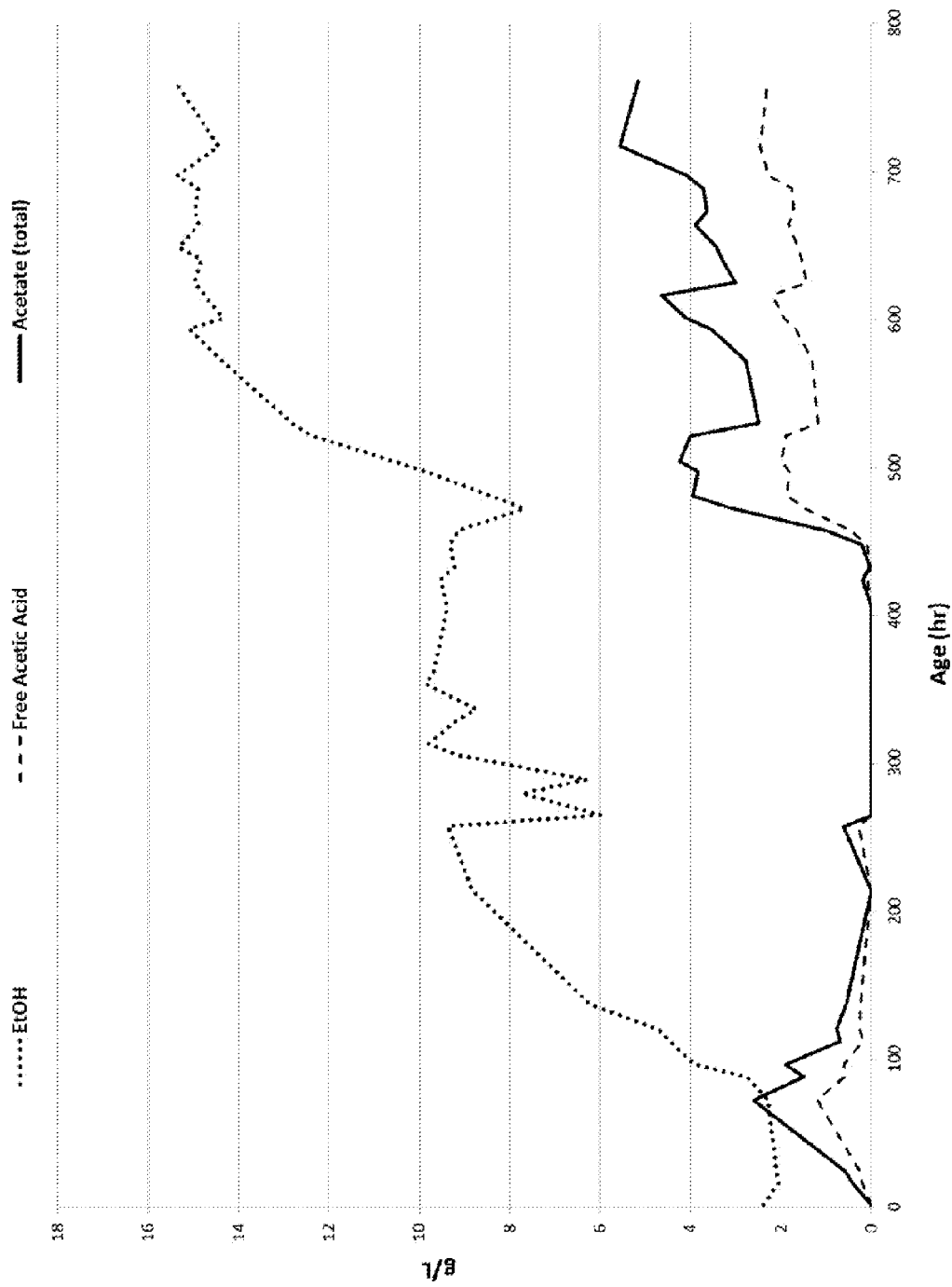

FIG. 6 shows a plot of the recovery of products for the 0 to 760 hour run phase. Overall the results of the product analysis show a high concentration of ethanol in the fermenter throughout the run phase despite the elimination of cysteine addition to the liquid media feed. Ethanol concentration increased significantly at the step up on the gas flow rate despite the elimination of all serine addition. The product data also shows a very low productivity of free acetic acid and total acetate at the start of the run phase, but with higher concentrations at the higher gas flow rates and the elimination of serine the acetate concentrations increased. Throughout the run phase butanol and butyrate production were below 0.3 g/l.

Example 5

A seed culture comprising the PETC strain of *Clostridium ljungdahlii* obtained from ATCC and having ATCC Number 55383 was grown in a seed vessel and then introduced into the fermentor at the beginning of the continuous fermentation run according to the General Procedures as previously described herein. At the initiation of the run (hour 0) the base liquid media entering the fermenter contained cysteine at an average concentration of 1.2 mM (~0.4 mM/day/OD) to provide 1× of an amino acid and sulfur constituent. Metabisulfite addition to the liquid media began at hour 533 at an average concentration of 0.3 mM (~0.03 mM/day/OD) to provide a 0.25× addition of metabisulfite, and a 0.5× addition of sulfur atoms. DTPA was used as a chelant in this run at a concentration of 0.79 g/L. Gas flow was brought up to 200 mL/min over about the first 200 hours of the run phase and then adjusted between a range of about 200 to 250 mL/min over the rest of the run phase. The gas had a volumetric composition of 29-31% CO, 18-19% $CO_2$, 39-41% $H_2$ and 11% methane. After establishment of the run, base liquid media addition varied within a range of about 2 to 2.9 liters per day. Pressure was increased over the first 30 hours and then maintained at 930 mbar throughout the run phase and the temperature remained at approximately 37° C. At hour 644 the cysteine addition stopped. At hour 700 the addition rate of metabisulfite was raised to an average of 0.4 mM (~0.04 mM/day/OD) to provide a 0.35× addition. At about hour 920, the addition rate of metabisulfite was raised to an average of 0.5 mM (~0.07 mM/day/OD) to provide a 0.45× additiona and remained at the level throughout the rest of the run phase. The pH in the fermenter was maintained at 5.3 through hour 814 at then gradually decreased until reaching 5.0 at about hour 900 and remained between 4.9 and 5.1 for the rest of run.

Figure 7:
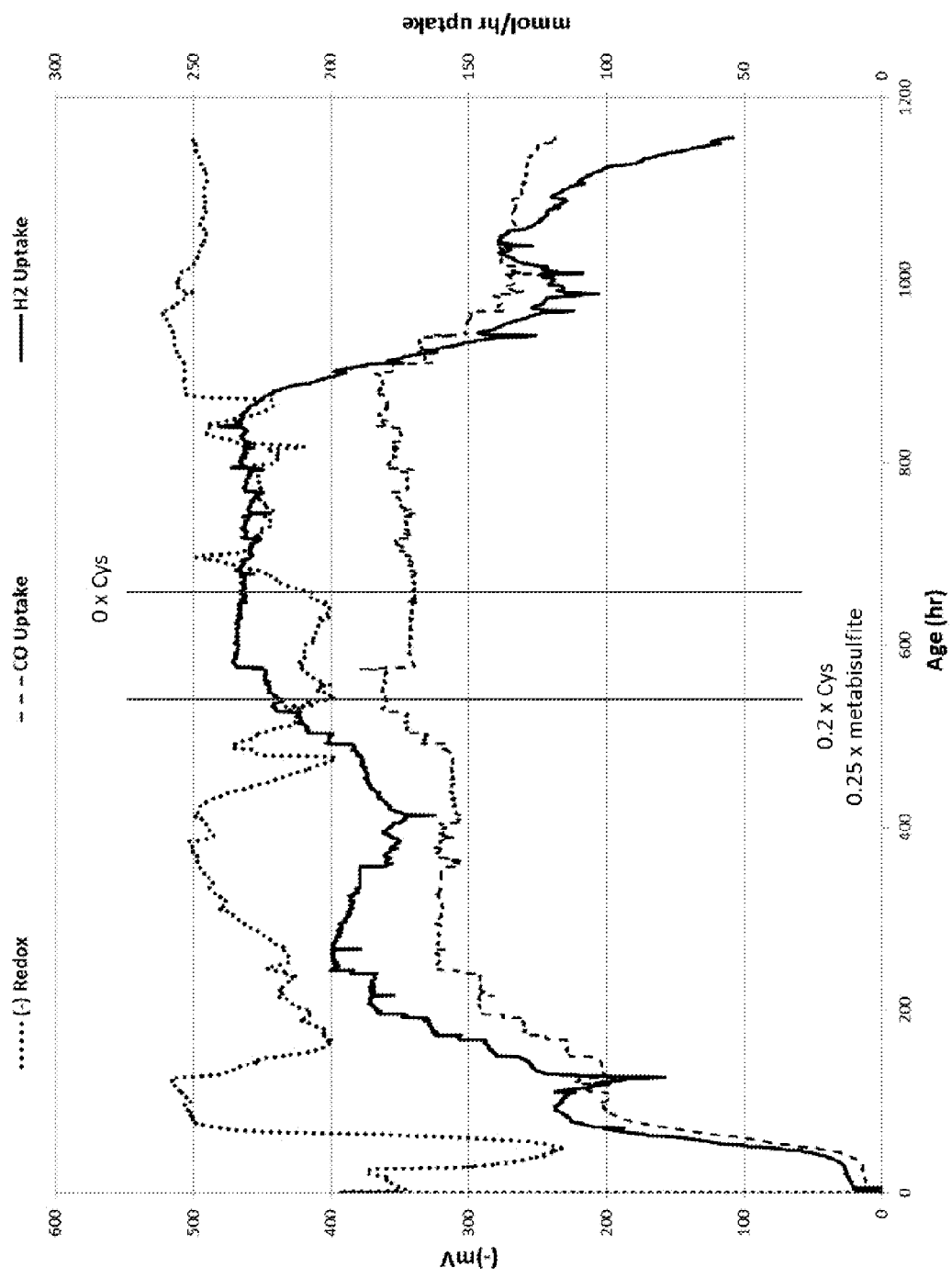

FIG. 7 shows the operational values for the phase of the run starting from hour 0 through 1150 hours. After initial ramp-up, the agitation for the run remained relatively constant in a range of between 400 and 425 rpm. FIG. 7 shows a very stable uptake of CO and hydrogen after initiation of the run and through the first 900 hour run phase. The uptake of CO was stable and continued for over 250 hours after all addition of cysteine was stopped. Hydrogen uptake also remained relatively stable for 200 hours following removal of all cysteine addition. Colorimetric analysis of the off-gas also showed hydrogen sulfide in the range of 0 to 350 ppm.

Figure 8:
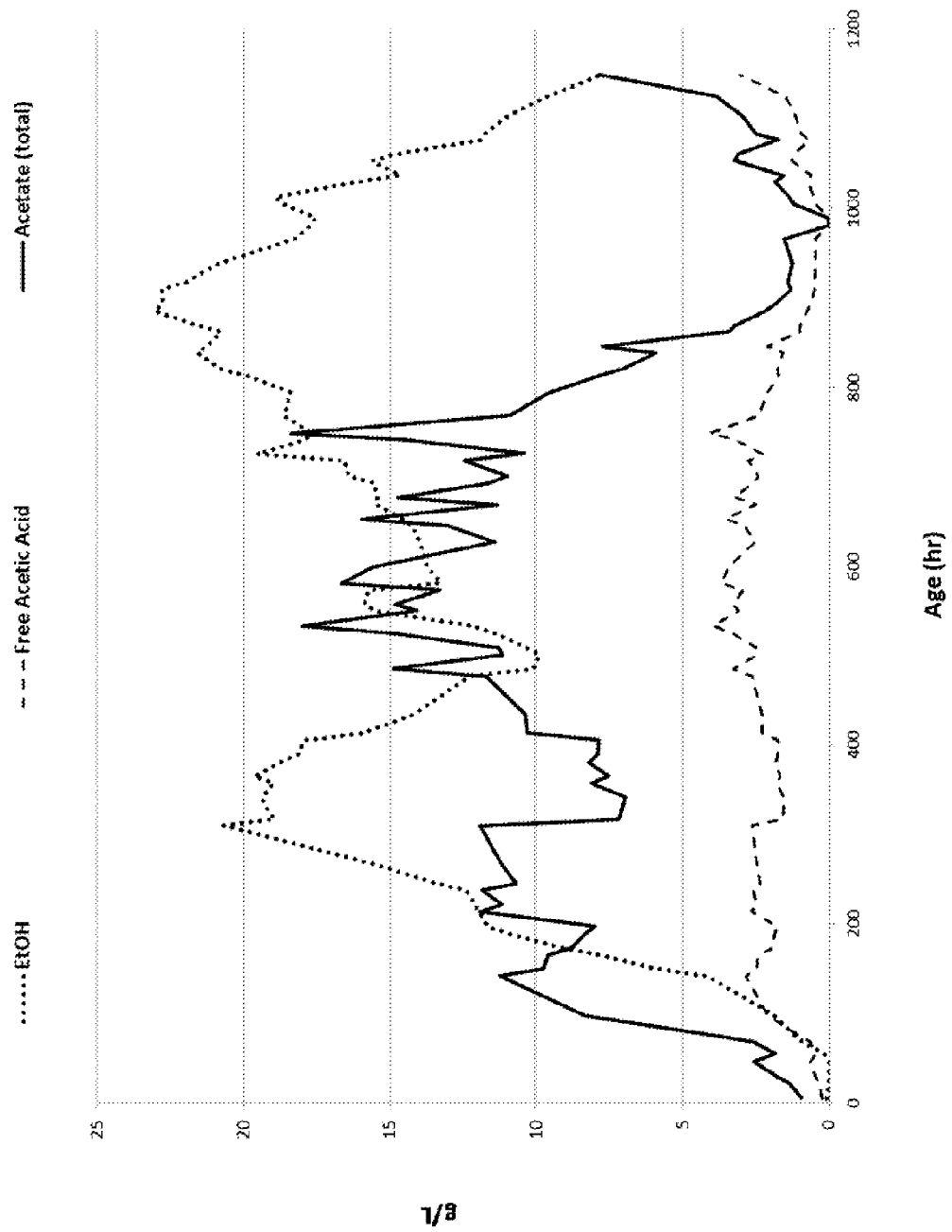

FIG. 8 shows a plot of the recovery of products for the 1150 hours of the run. The results of the product analysis show that the fermenter continued to produce a very high titer of combined ethanol and acetate products. It was also noted that the elimination of the cysteine appeared to improve the selectivity of the fermenter to produce ethanol. Except for a spike of free acetic acid at about hour 500, the product data also shows a relatively low productivity of free acetic acid throughout the run. This spike coincided with the transition from cysteine as sulfur source to metabisulfite as sulfur source. Throughout the run phase butanol and butyrate production were below 0.22 g/L.

Example 6

A seed culture comprising *Clostridium coskatii* obtained from the same cryostock as described in Example 1 was grown in a seed vessel and then introduced into the fermentor at the beginning of the continuous fermentation run according to the General Procedures as previously described herein. At the initiation of the run (hour 0) the base liquid media entering the fermenter contained cysteine at an average concentration of 1.2 mM (~0.14 mM/day/OD) to provide 1× of an amino acid and sulfur constituent. At hour 172 the cysteine addition rate was lowered to an average of 0.24 mM (~0.02 mM/day/OD) to provide a 0.2× addition of sulfur to the media and sulfurous acid addition to the liquid media was initiated at an average concentration of 0.3 mM (~0.03 mM/day/OD) to provide a 0.25× addition of sulfur atoms. DTPA was used as a chelant in this run at a concentration of 0.79 g/L. Gas flow was brought up over about the first 150 hours to a rate of about 200 to 230 mL/min and stayed in this range throughout the run. The gas had a volumetric composition of 29-31% CO, 18-19% $CO_2$, 39-41% $H_2$ and 11-12% $CH_4$. After the run was established base liquid media addition was varied within a range of about 2.8 to 2.9 liters per day until about hour 511 when it was increased to a range of about 3.3 to 3.4 liters per day. Pressure was increased over the first 50 hours and then maintained at 930 mbar throughout the run phase and temperature remained at approximately 37° C. At hour 283 the cysteine addition rate was dropped to zero and the sulfurous acid addition was raised to an average of 0.6 mM (~0.07 mM/day/OD) for a 0.5× sulfur addition for the remainder of the run. The pH in the fermenter was maintained at value of about 5.3 until about hour 350, then lowered to about 5.0 until hour 450 and thereafter was kept in a range of 4.9 to 4.6 for throughout this phase of the run.

Figure 9:
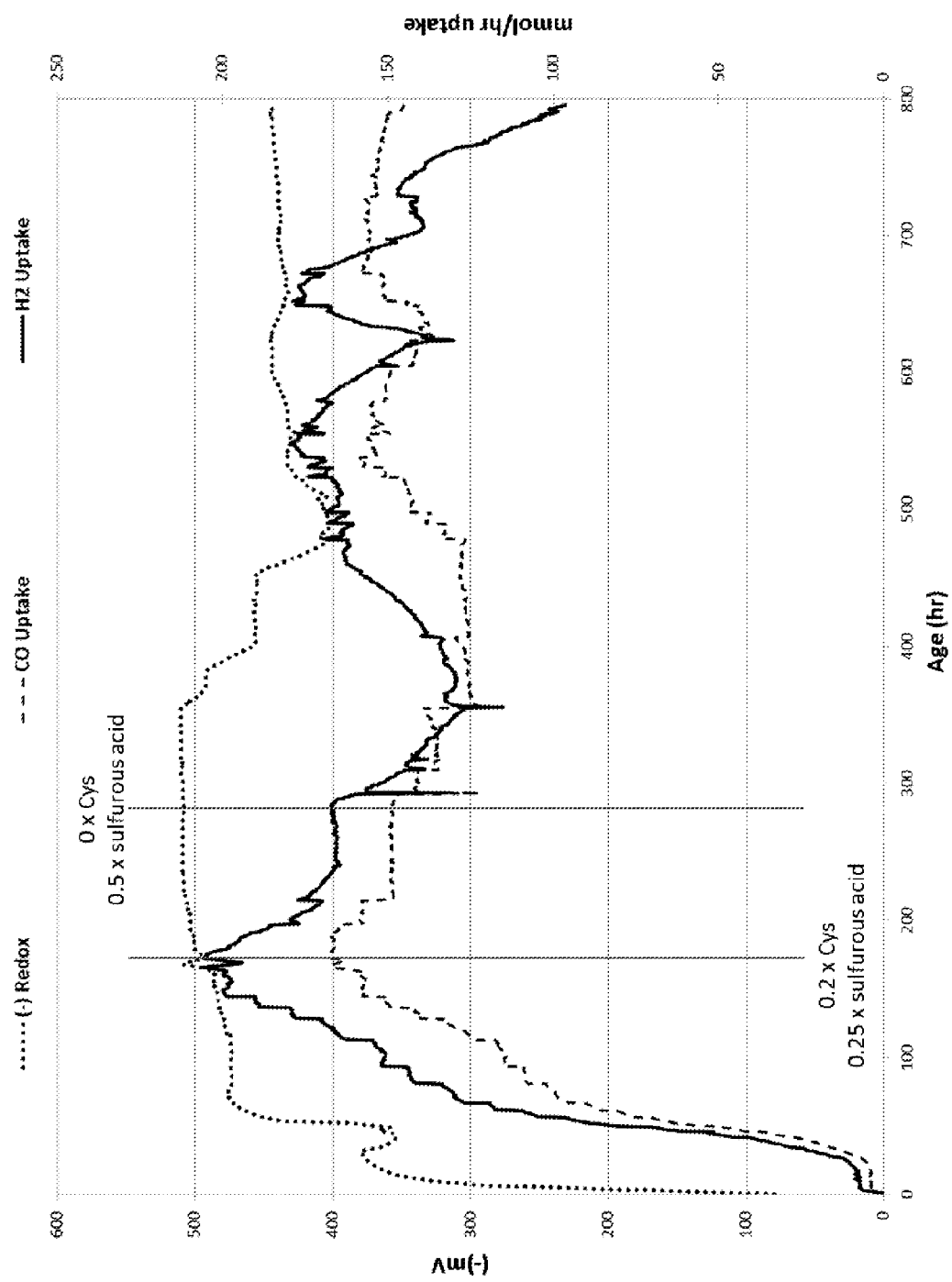

FIG. 9 shows the operational values for the phase of the run starting from hours 0 through 788. After initial ramp-up, the agitation for the run remained in a range from 420 to 435 rpm. FIG. 9 shows relatively steady uptake of CO following hour 200 when the fermentation stabilized from the changes in the sulfur source and the elimination of cysteine. Once the fermentation was established hydrogen uptake remained at relatively high level until the very end of the run. Thus good utilization of the CO and hydrogen was found to occur after the removal of cysteine from the liquid media. Colorimetric analysis of the off-gas also showed hydrogen sulfide in the range of 0 to 153 ppm.

Figure 10:
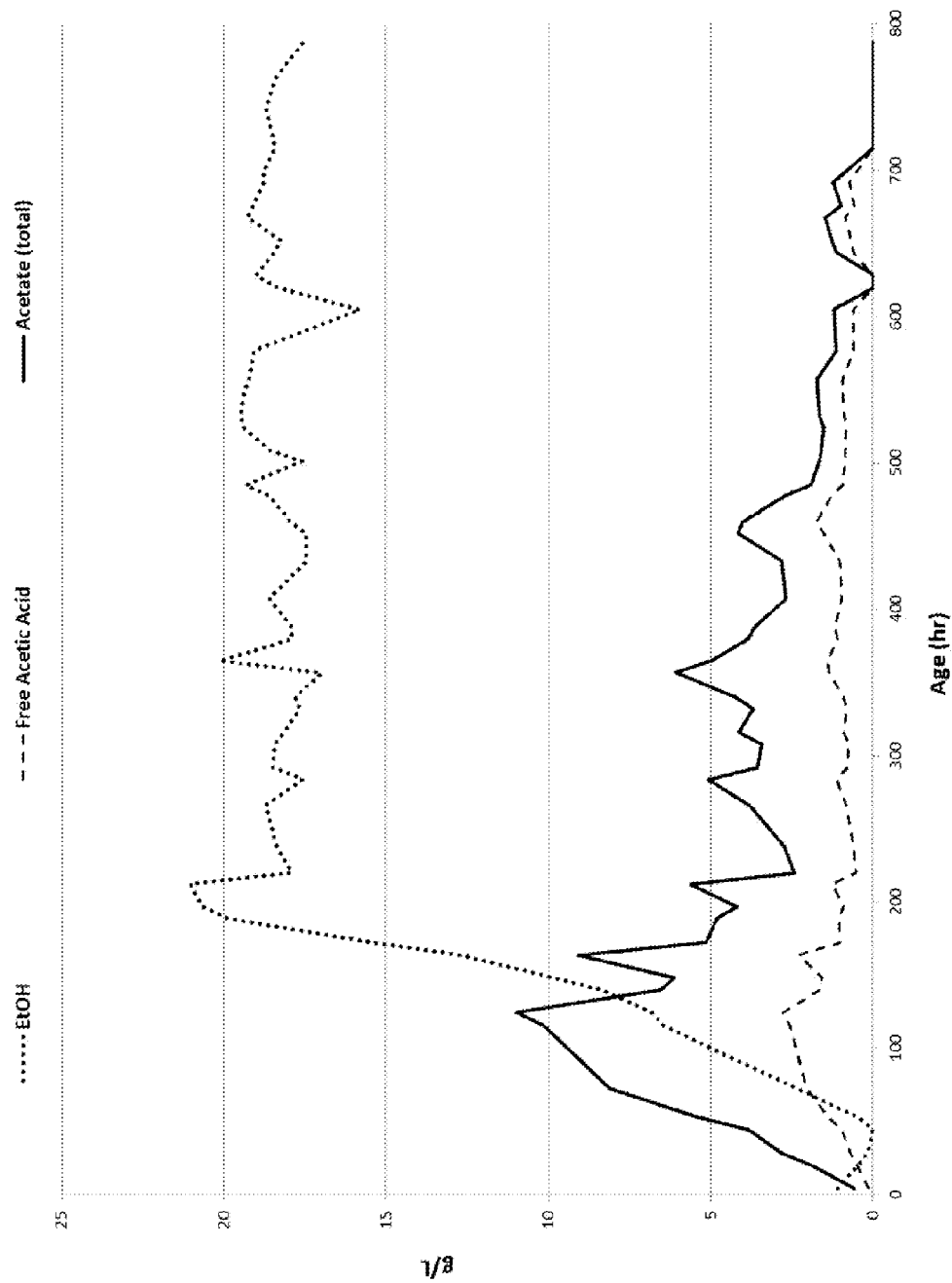

FIG. 10 shows a plot of the recovery of products for the 0 to 788 hour run phase. The results of the product analysis show that the fermentation produced a high concentration of ethanol within the first 200 hours. The concentration of ethanol in the fermenter remained in the same high range after the elimination of the cysteine from the liquid media and until the end of the run. The product data also shows a high concentration of free acetic acid and total acetate at the start of the run phase that diminished as the ethanol concentration increased. Throughout the run phase butanol and butyrate production were below the detection limit of the GC.

Example 7

A seed culture comprising *Clostridium coskatii* obtained from the same cryostock as described in Example 1 was grown in a seed vessel and then introduced into the fermentor at the beginning of the continuous fermentation run according to the General Procedures as previously described herein. At the initiation of the run (hour 0) the base liquid media entering the fermenter contained cysteine at an average concentration of 1.2 mM to provide 1× of an amino acid and sulfur constituent. At hour 172 the cysteine addition rate was lowered to an average of 0.24 mM to provide a 0.2× addition of sulfur to the liquid media and bisulfite addition to the liquid media was initiated at an average concentration of about 0.4 mM (~0.04 mM/day/OD) to provide a 0.33× addition of sulfur atoms. DTPA was used in this run as a chelant from hour 0-818 at a concentration of 0.079 g/L. After hour 818 no chelant was used. Gas flow was brought up at this point to about 230 mL/min and kept in range of from 200 to 250 mL/min until about 800 hours after which it was brought up to about 300 mL/min where it remained for the rest of the phase of the run. The gas had a volumetric composition of 29-31% CO, 18-19% $CO_2$, 39-41% H2 and 11-12% $CH_4$. After establishment of the run the base liquid media addition was varied within a range of about 2.5 to 2.9 liters per day until about hour 509 when it was increased to a range of about 3.3 to 3.4. Pressure was increased over the first 50 hours and then maintained at 930 mbar throughout the run phase and temperature remained at approximately 37° C. At hour 283 the cysteine addition rate was dropped to zero and the bisulfite addition was raised to an average of 0.8 mM (~0.1 mM/day/OD) for a 0.66× concentration until hour 988 when it was raised to about 1.6 mM (~0.2 mM/day/OD) for a 1.33× concentration for the rest of the run phase. The pH in the fermenter was maintained at 5.3 until about hour 400, then lowered to about 5.0 until hour 620 and thereafter was kept at 4.7 for the remaining phase of the run.

Figure 11:
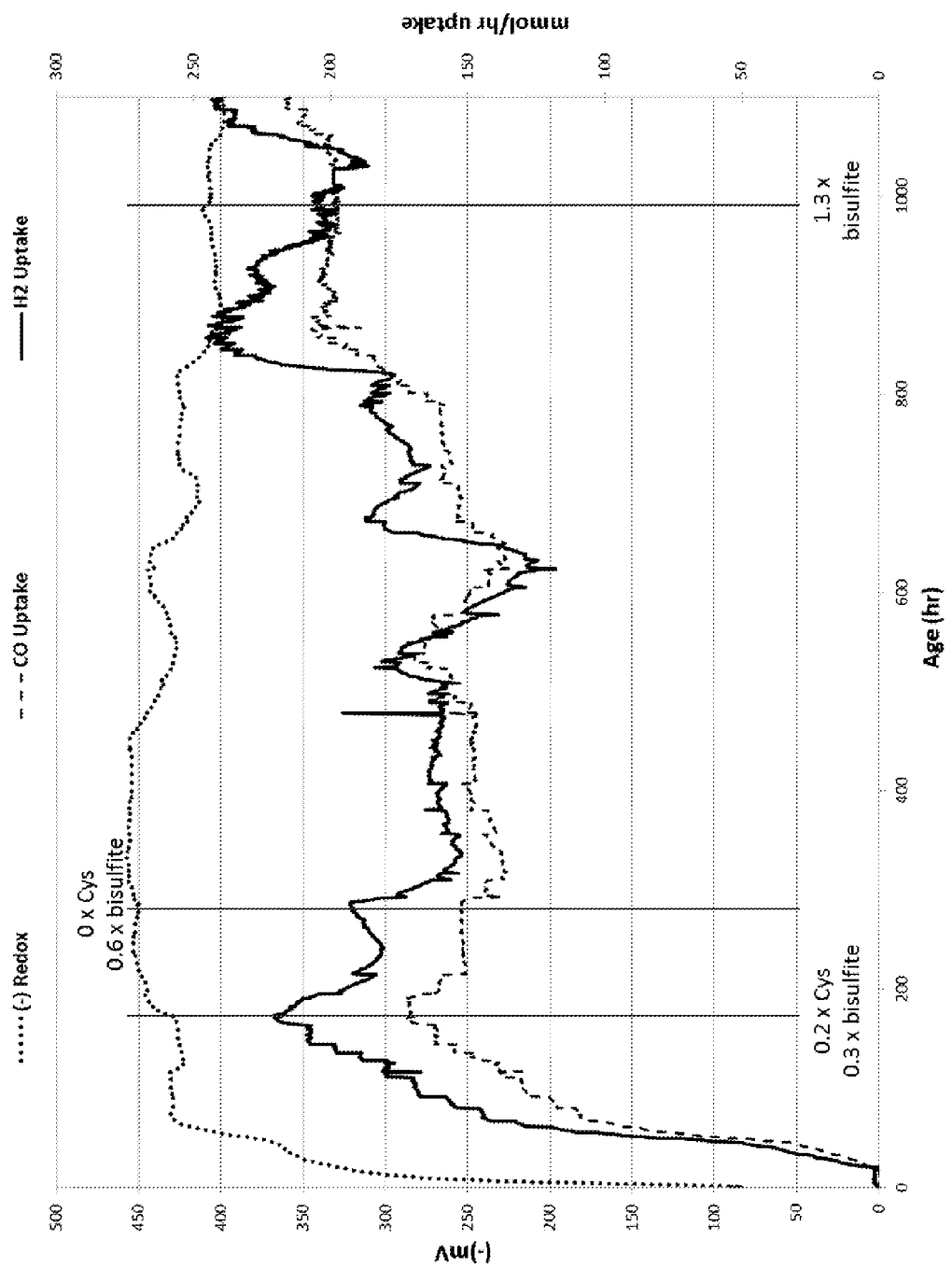
Figure 12:
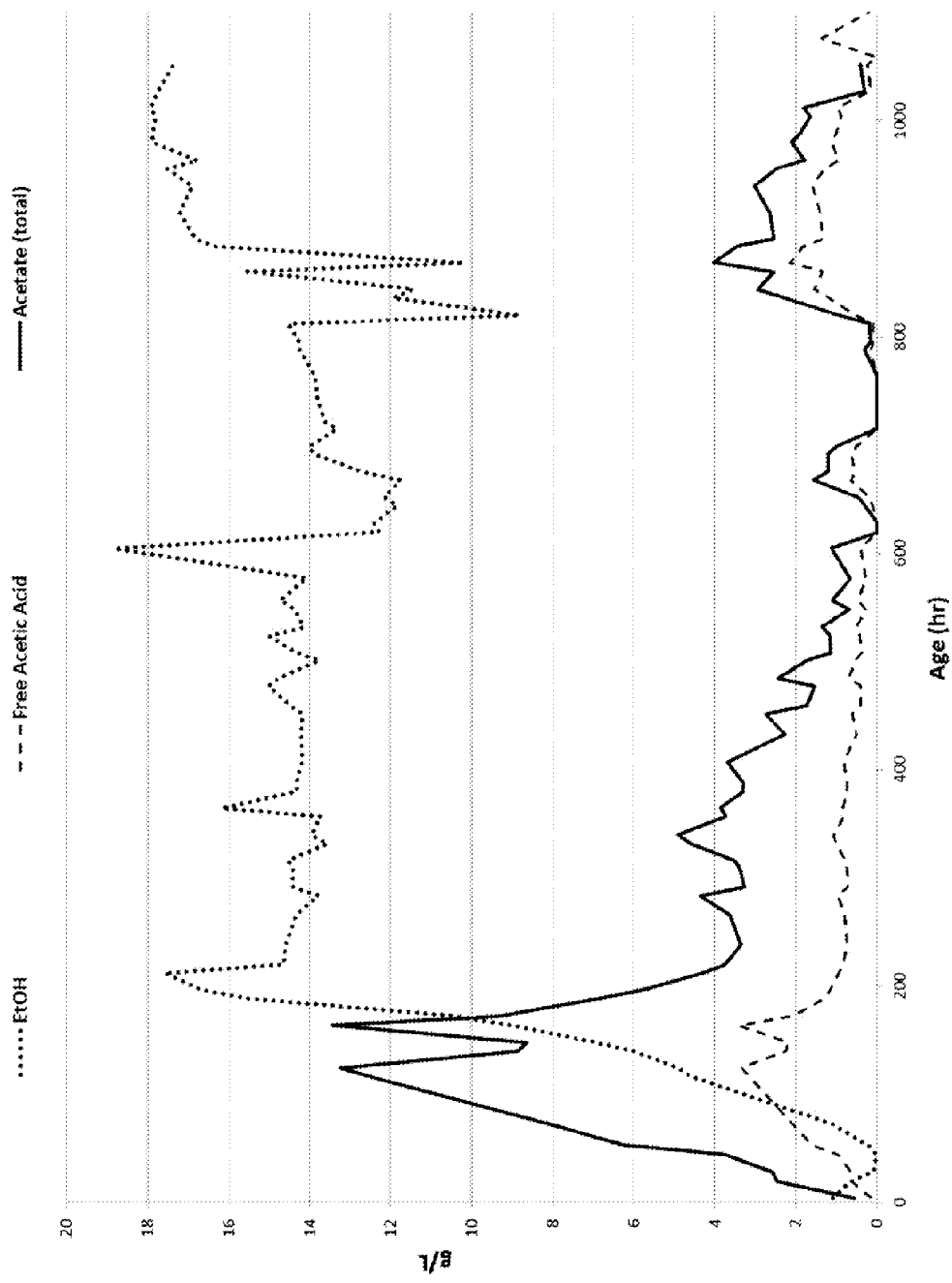

FIG. 11 shows the operational values for the phase of the run starting from hour 0 through 1100 hours. After initial ramp-up, the agitation for the run phase remained in a range of from 400 to 435 rpm. FIG. 9 shows the fermenter reaching a high uptake of CO at about hour 200 with a general increase of CO uptake throughout the run phase even after the elimination of cysteine. The hydrogen uptake generally tracked the CO uptake but with greater variability with both uptake measurements demonstrating the fermenter ability to utilize higher gas flow without the continued addition of cysteine to the liquid media. After hour 1100 both CO uptake and hydrogen uptake fell off sharply and the run was subsequently terminated. Colorimetric analysis of the off-gas also showed hydrogen sulfide in the range of 17 to 206 ppm. FIG. 12 shows a plot of the recovery of products for the same run phase. The results of the product analysis show that the fermentation produced a concentration of ethanol within the first 200 hours. The concentration of ethanol in the fermenter remained in the same high range after the elimination of the cysteine from the liquid media and until the end of the run phase when the run became unstable. The product data also shows a high concentration of free acetic acid and total acetate at the start of the run phase that diminished as the ethanol concentration increased.

Example 8

A seed culture comprising *Clostridium coskatii* obtained from the same cryostock as described in Example 1 was grown in a seed vessel and then introduced into the fermentor at the beginning of the continuous fermentation run according to the General Procedures as previously described herein. At the initiation of the run (hour 0) the base liquid media entering the fermenter contained cysteine at an average concentration of 1.2 mM to provide a 1× of an amino acid and sulfur constituent. At hour 172 the cysteine addition rate was lowered to an average of about 0.24 mM to provide a 0.2× addition of sulfur to the liquid media and metabisulfite addition to the liquid media was initiated at an average concentration of about 0.3 mM (~0.03 mM/day/OD) to provide a 0.25× addition of sulfur atoms. DTPA was used as a chelant in this run at a concentration of 0.79 g/L from hour 0 to 796. No chelant was used after hour 796. Gas flow was brought up at this point to about 230 mL/min and kept in range of from 180 to 230 mL/min until about 800 hours after which it was brought up to about 300 mL/min where it remained for the rest of the phase of the run. The gas had a volumetric composition of 29-31% CO, 18-19% $CO_2$, 39-41% $H_2$ and 11-12% $CH_4$. After the run was established base liquid media addition was varied within a range of about 2.5 to 2.9 liters per day for about the first 500 hours and then to a range of about 3.3 to 4.0 liters per day. Base liquid media addition was varied within a range of about 2.2 to 3.0 liter per day. Pressure was increased over the first 50 hours and then maintained at 930 mbar throughout the run phase and temperature remained at approximately 37° C. At hour 283 the cysteine addition rate was dropped to zero. At hour 340 the metabisulfite addition was raised to an average of about 0.4 mM (~0.06 mM/day/OD) for a 0.35× addition of metabisulfite and a 0.7× addition of sulfur until hour 548 when it was raised to about 0.54 mM for a 0.45× addition of metabisulfite and 0.9× addition of sulfur for the rest of the run phase. The pH in the fermenter was maintained at value of about 5.3 until about hour 170, then raised to about 5.4 until about hour 215 when it returned to 5.3 and remained there until about hour 360 after which it was gradually lowered to a range of from 4.5 to 4.7 for the remaining phase of the run.

Figure 13:
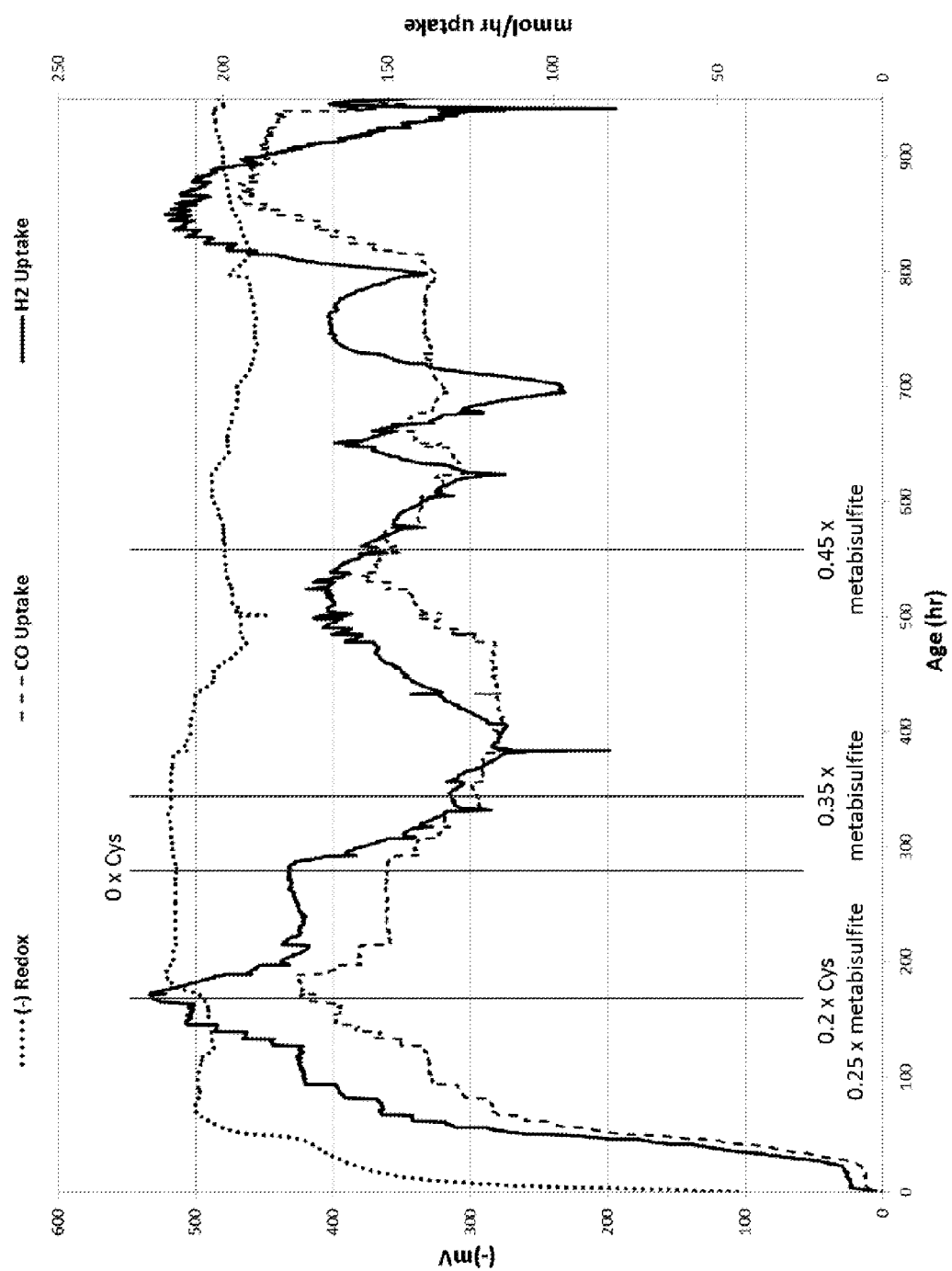
Figure 14:
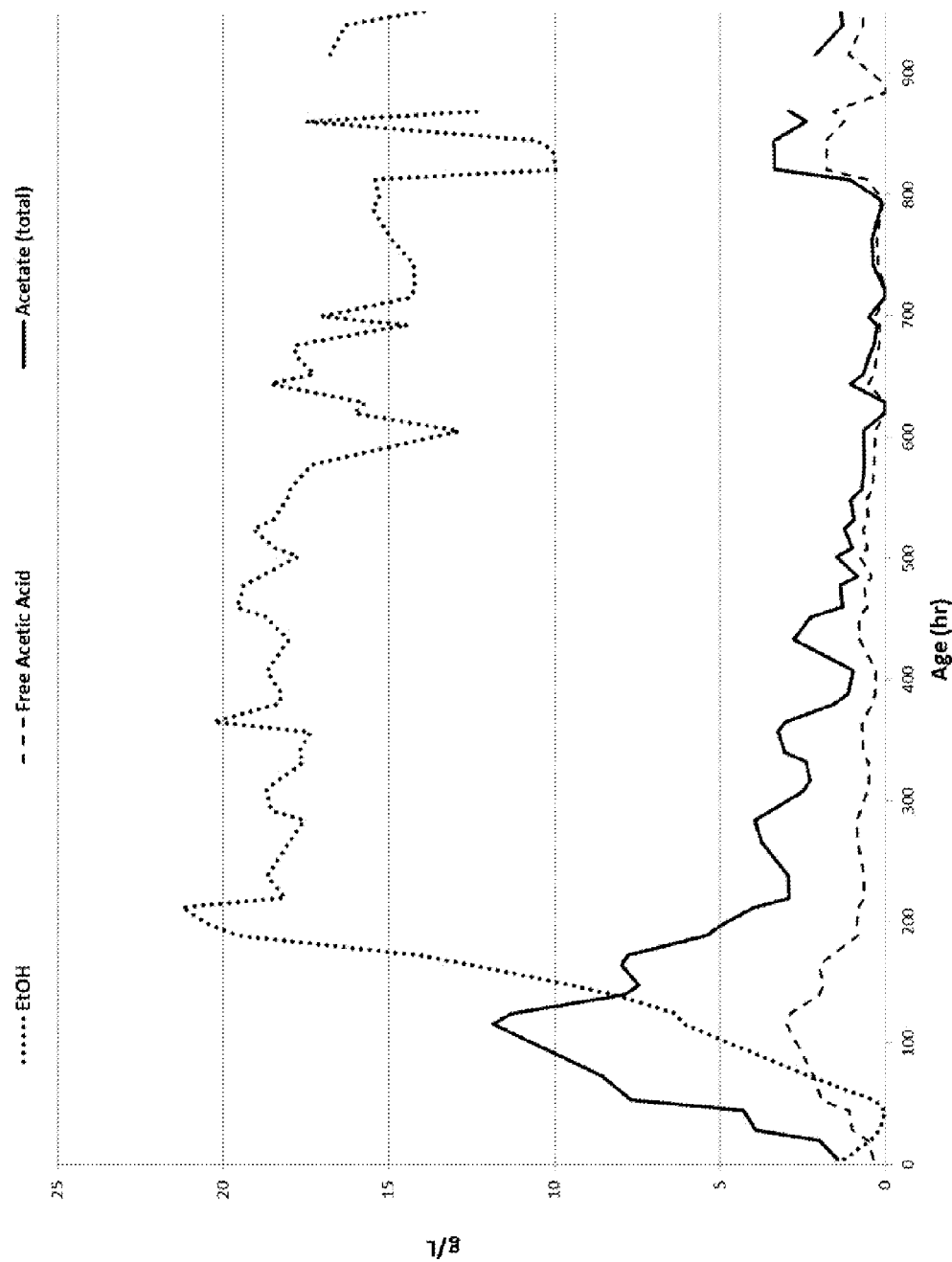

FIG. 13 shows the operational values for the phase of the run starting from hour 0 through 950 hours. After initial ramp-up, the agitation for the run phase remained in a range of from 390 to 420 rpm. FIG. 13 shows the fermenter reaching a high uptake of CO and hydrogen at about hour 173. CO and hydrogen uptake persisted throughout the run phase even after the elimination of cysteine. The hydrogen uptake generally tracked the CO uptake but with greater variability with both measures demonstrating the fermenter ability to utilize higher gas flow without the continued addition of cysteine to the liquid media. After hour 1100 both CO uptake and hydrogen uptake fell off sharply and the run was subsequently terminated. Colorimetric analysis of the off-gas also showed hydrogen sulfide in the range of 18 to 200 ppm. FIG. 14 shows a plot of the recovery of products for the same run phase. The results of the product analysis show that the fermentation produced a concentration of ethanol within the first 200 hours. The concentration of ethanol in the fermenter remained in the same high range after the elimination of the cysteine from the liquid media and until the end of the run phase when the run became unstable. The product data also shows a high concentration of free acetic acid and total acetate at the start of the run phase that diminished as the ethanol concentration increased. Throughout most of the run phase butanol and butyrate production were detection limit of the gas chromatograph (~0.1 g/l).

Example 9

A seed culture comprising *Clostridium autoethanogenum* obtained from the microorganism collection of DSMZ and having a DSM No. 10061 was grown in a seed vessel and then introduced into the fermentor at the beginning of the continuous fermentation run according to the General Procedures as previously described herein. At the initiation of the run (hour 0) the base liquid media entering the fermenter contained cysteine at an average concentration of 1.2 mM to provide 1× of an amino acid and sulfur constituent. At hour 150 the cysteine addition rate was lowered to an average of about 0.24 mM to provide a 0.2× addition of sulfur from cysteine to the liquid media and metabisulfite addition to the liquid media was initiated at an average concentration of about 0.3 mM (~0.04 mM/day/OD) to provide a 0.5× addition of sulfur atoms. DTPA was used as a chelant in this run at a concentration of 0.79 g/L. At hour 144 gas flow was brought up at this point to about 220 mL/min and kept in range of from 220 to 240 mL/min until about 500 hours after which the run became unstable and was terminated. The gas had an average volumetric composition of 29-30% CO, 17-19% $CO_2$, 39-41% $H_2$ and 11-12% $CH_4$. Base liquid media addition was varied within a range of about 2.8 to 2.9 liters per day. Pressure was increased over the first 30 hours and then maintained at 930 mbar throughout the run phase and temperature remained at approximately 37° C. At hour 262 the cysteine addition rate was dropped to zero. The pH in the fermenter was maintained at a value of about 5.3 until about hour 431, then gradually lowered throughout the run phase to about 4.9.

Figure 15:
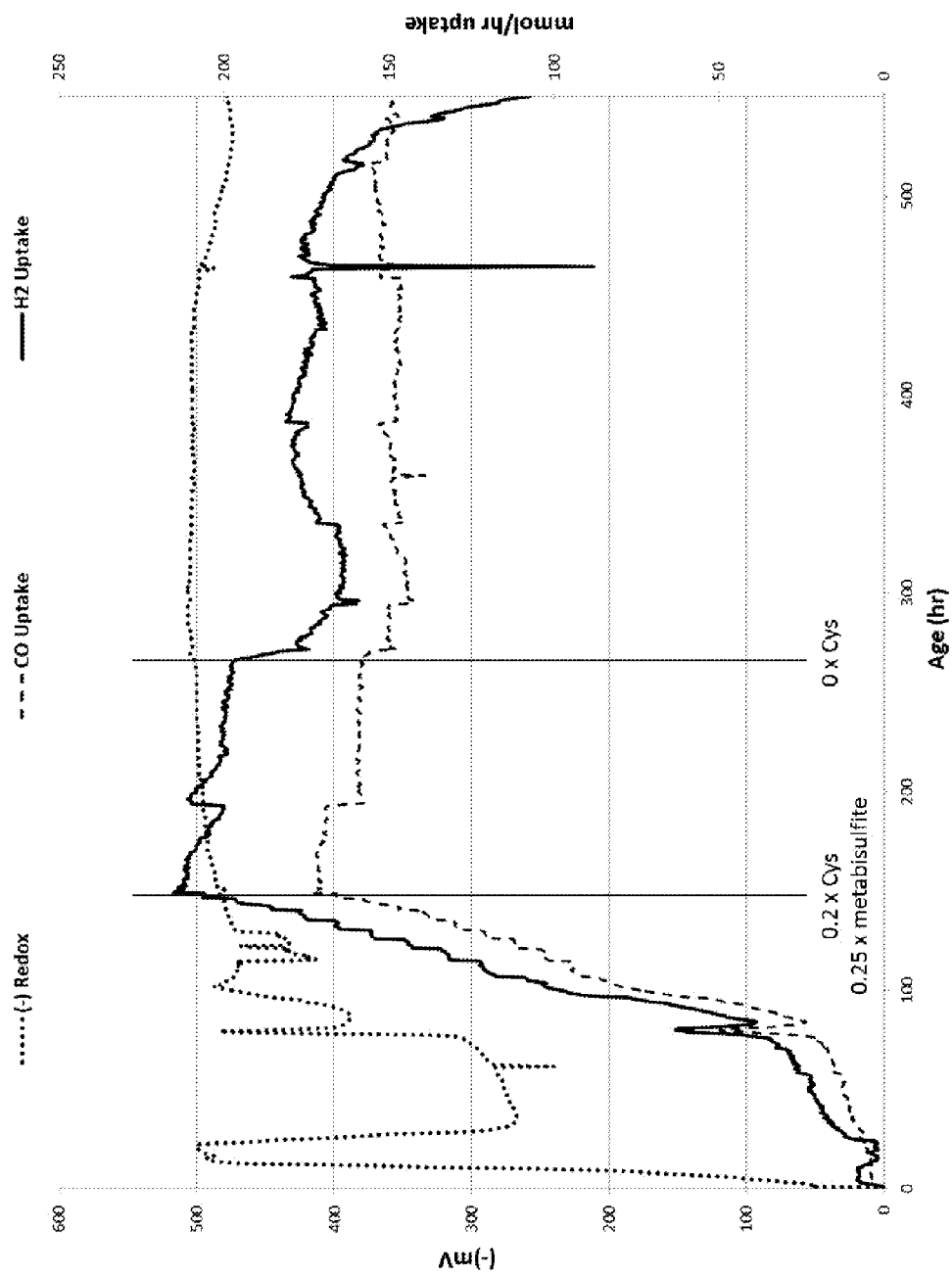
Figure 16:
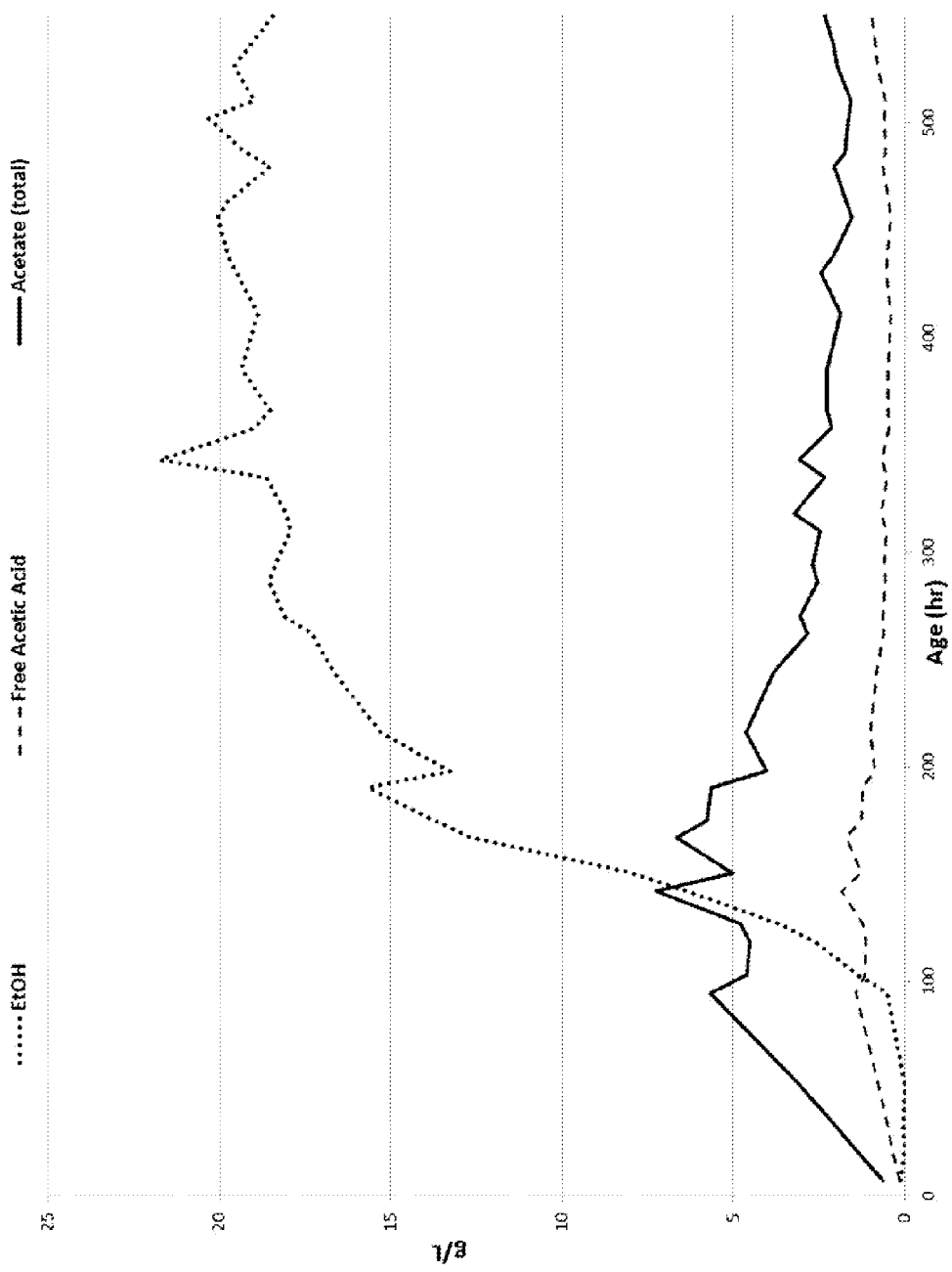

FIG. 15 shows the operational values for the phase of the run starting from hour 0 through 900 hours. After initial ramp-up, the agitation for the run phase remained in a range of from 415 to 425 rpm. FIG. 15 shows the fermenter reaching its highest uptake of CO at about hour 150 with a lowered but still high and stable uptake of CO throughout the rest of this phase of the run even after the elimination of cysteine. The hydrogen uptake generally tracked the CO uptake but with greater variability with both measures demonstrating the fermenter ability to a high gas uptake without the addition of cysteine to the liquid media. After hour 550 both CO uptake and hydrogen uptake fell off sharply and the run was subsequently terminated. Colorimetric analysis of the off-gas also showed hydrogen sulfide in the range of 0 to 335 ppm. FIG. 16 shows a plot of the recovery of products for the same run phase. The results of the product analysis show that the fermentation produced a concentration of ethanol within the first 200 hours. The concentration of ethanol in the fermenter remained in the same high range after the elimination of the cysteine from the liquid media and until the end of the run phase when the run became unstable. The product data also shows a high concentration of total acetate at the start of the run phase that diminished as the ethanol concentration increased. Throughout most of the run phase butanol and butyrate production were below the detection limits of the GC.

Example 10

A seed culture comprising *Clostridium coskatii* obtained from the same cryostock as described in Example 1 was grown in a seed vessel and then introduced into the fermentor at the beginning of the continuous fermentation run according to the General Procedures as previously described herein except the fermentor was a Biostat B Plus and was maintained at 1 atm of pressure. At the initiation of the run (hour 0) the base liquid media in the vessel contained 0.12 mM bisulfite, for a 0.1× sulfur addition and contained no cysteine other than cysteine that was present with the culture as it was transferred from the seed vessel. The media feed for the run contained bisulfite at a concentration of 0.6 mM over the course of the run to provide a 0.5× of sulfur atoms. DTPA was used as a chelant in this run at a concentration of 0.79 g/L hours 0 to 318. No chelant was used after hour 318. Gas flow for this run was rapidly brought up to 100 mL/min and at hour 242 was raised to 200 mL/min and remained at the level through the first 600 hour phase of the run. The gas had an average volumetric composition of 29-30% CO, 17-18% $CO_2$, 40-41% $H_2$ and 11% $CH_4$. Base liquid media addition rate was kept at about 1 liter per day until hour 313 and was then raised to 2 liters per day for the rest of the run phase. The fermenter operated at ambient pressure throughout the run. Temperature remained at approximately 37° C. The pH in the fermenter was maintained at value of about 5.3 until about hour 214 when it was lowered to about 4.9 for the rest of the run.

Figure 17:
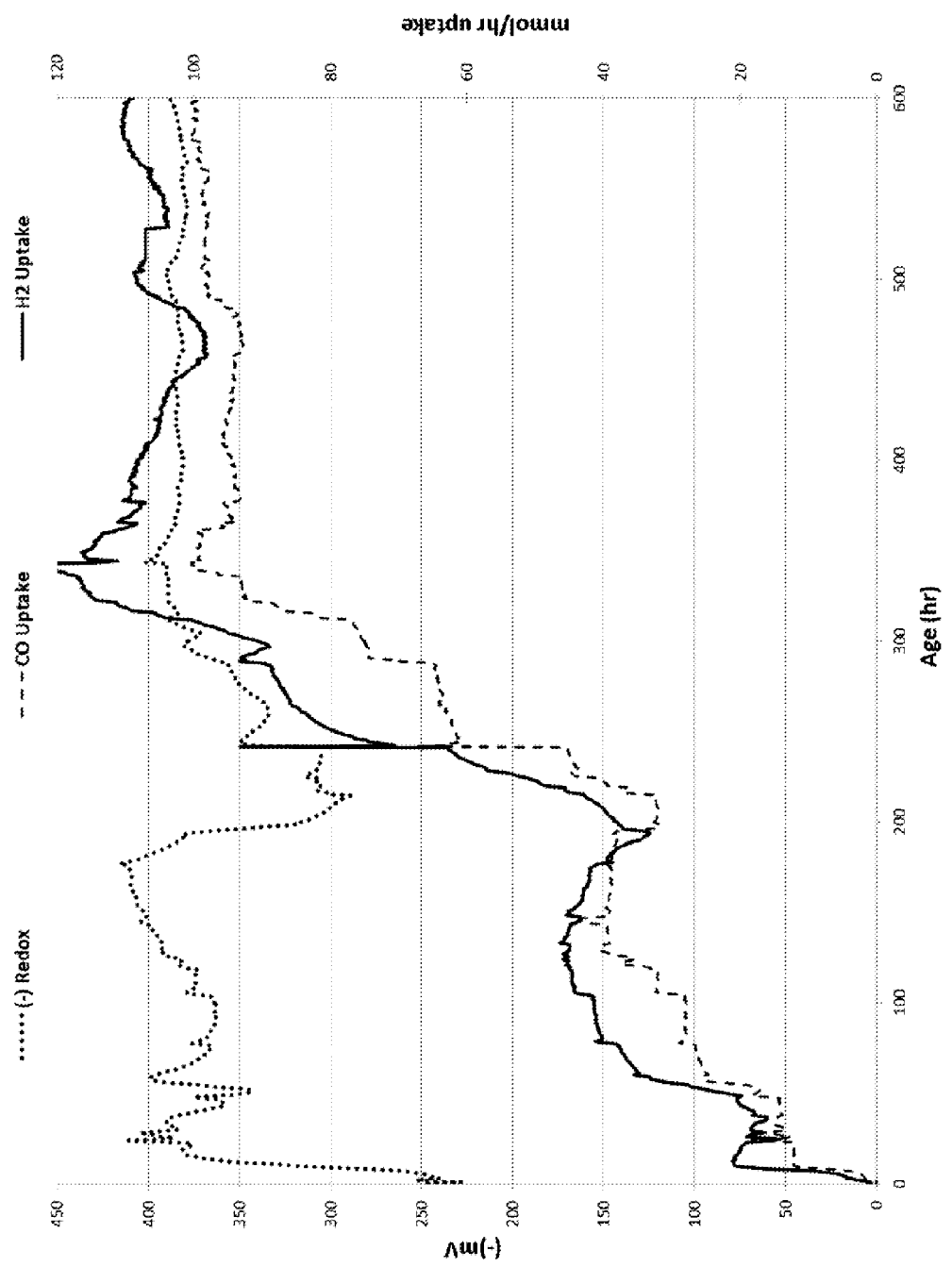

FIG. 17 shows the operational values for the phase of the run starting from hour 0 through 600 hours. After initiation of the run, the agitation of the fermenter was increased in stages from 375 rpm to 450 rpm until hour 195, then lowered for about 20 hours to 430 and then began increasing stepwise again until at about 350 hours reaching a range of from 425 to 520 where it remained for the rest of the depicted run phase. FIG. 17 shows the fermenter with a steady increase of CO and hydrogen uptake that reached a peak at about hour 350 and then leveled off for the remainder of the run phase. After 600 hours the run became unstable and was terminated shortly thereafter.

Figure 18:
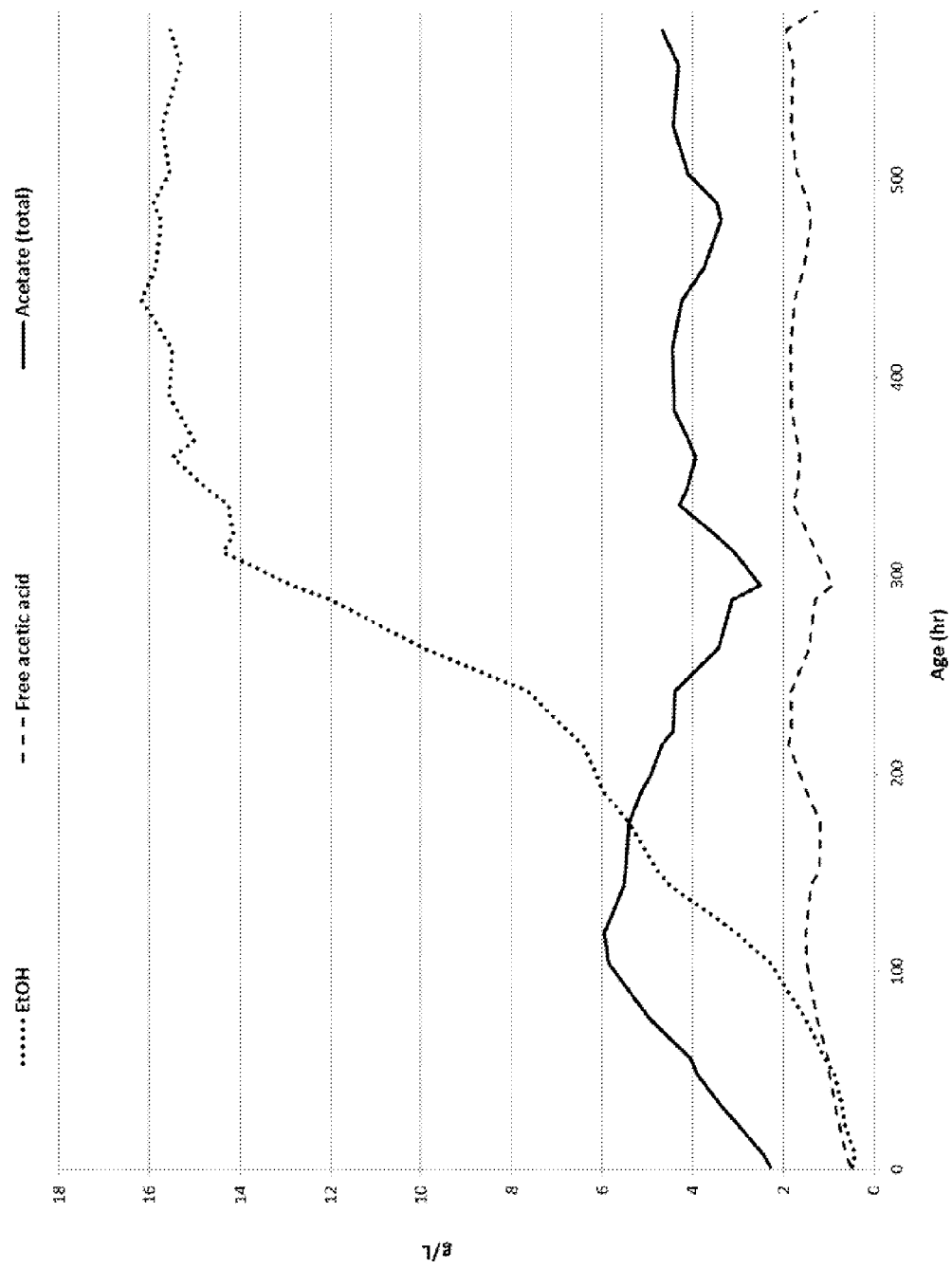

FIG. 18 shows a plot of the recovery of products for the same run phase. The results of the product analysis show that the fermentation produced ethanol at a steadily increasing concentration over the course of the run phase. The concentration of ethanol in the fermenter remained at its highest level for over 300 hours. The product data shows an elevated initial level of total acetate that stabilized at a lower level until the very end of the run phase. Throughout most of the run phase butanol and butyrate production were below detection limits of the GC. The depicted phase of the run shows that high concentrations of C2 oxygenates can be obtained with essentially only the addition of bisulfite as the sulfur source to the fermentation.

Example 11

A seed culture comprising *Clostridium coskatii* obtained from the same cryostock as described in Example 1 was grown in a seed vessel and then introduced into the fermentor at the beginning of the continuous fermentation run that was carried out according to the procedure as previously described herein For example, 10. At the initiation of the run (hour 0) the base liquid media entering the fermenter contained no cysteine other than cysteine that was present with the culture as it was transferred from the seed vessel. Bisulfite at a concentration of 0.6 mM was supplied via the media feed over the course of the run to provide 0.5× of sulfur atoms. The concentration of added bisulfite was raised to a 1× concentration for the final 40 hours of the run. DTPA was used as a chelant in this run at a concentration of 0.79 g/L from hours 0 to 122. No chelant was used after hour 122. Gas flow for this run was rapidly brought up to 100 mL/min and at hour 177 was raised to 120 mL/min over the next 20 hours and remained at the level until increasing at hour 312 to 130 mL/min for the remainder of the run. The gas had an average volumetric composition of 29-30% CO, 18% $CO_2$, 40-41% $H_2$ and 11% $CH_4$. Base liquid media addition rate was kept at about 1.25 liter per day until hour 313 per day and was then raised to 1.43 liters per day for the rest of the run. The fermenter operated at ambient pressure throughout the run. Temperature remained at approximately 37° C. The pH, except for a short spike to 5.1 at hour 122, was kept at 4.9 through hour 220, then lowered to 4.7 for about 40 hours, and returned to 4.8 at about 290 hours for the remainder of the run.

Figure 19:
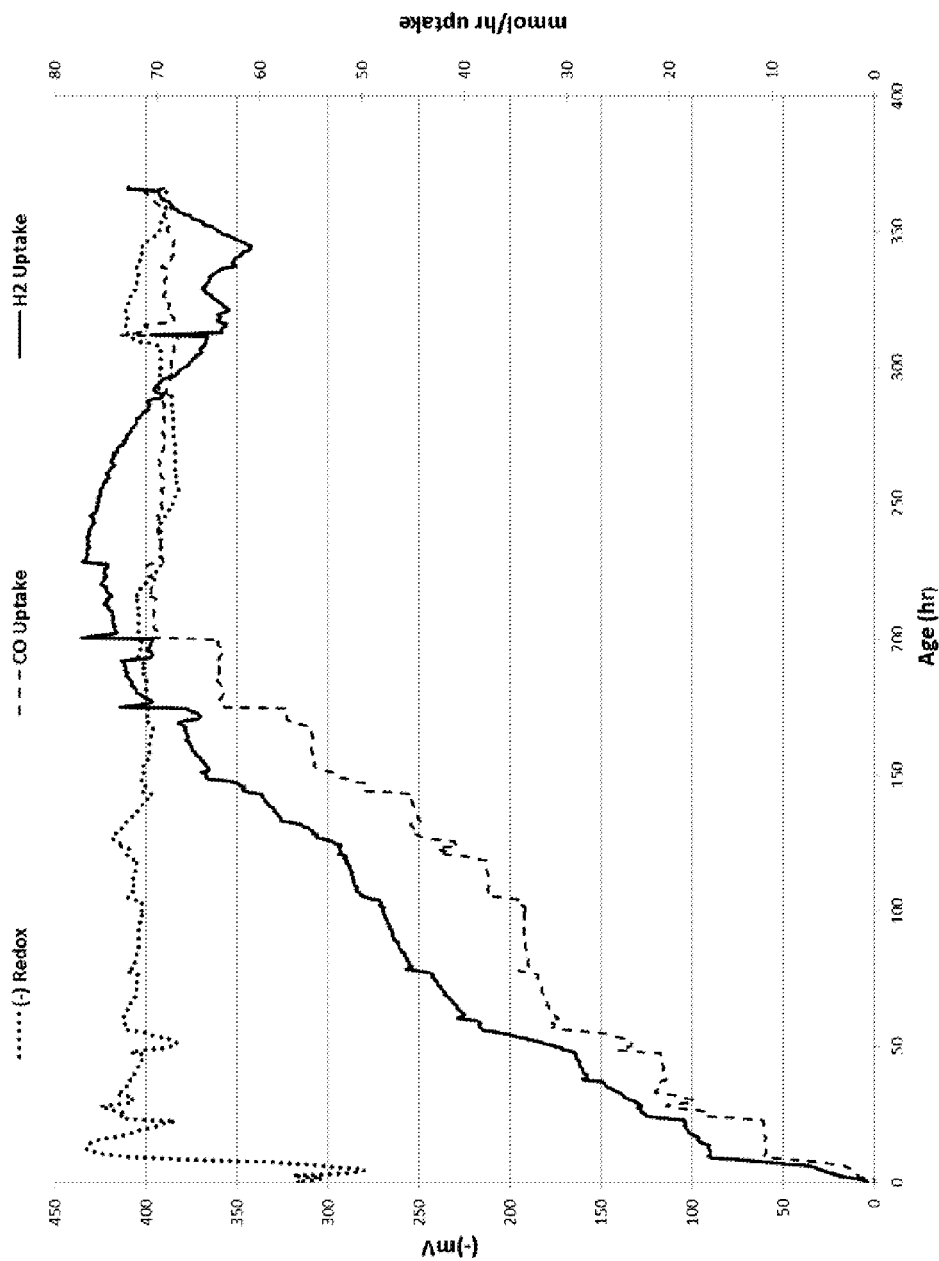
Figure 20:
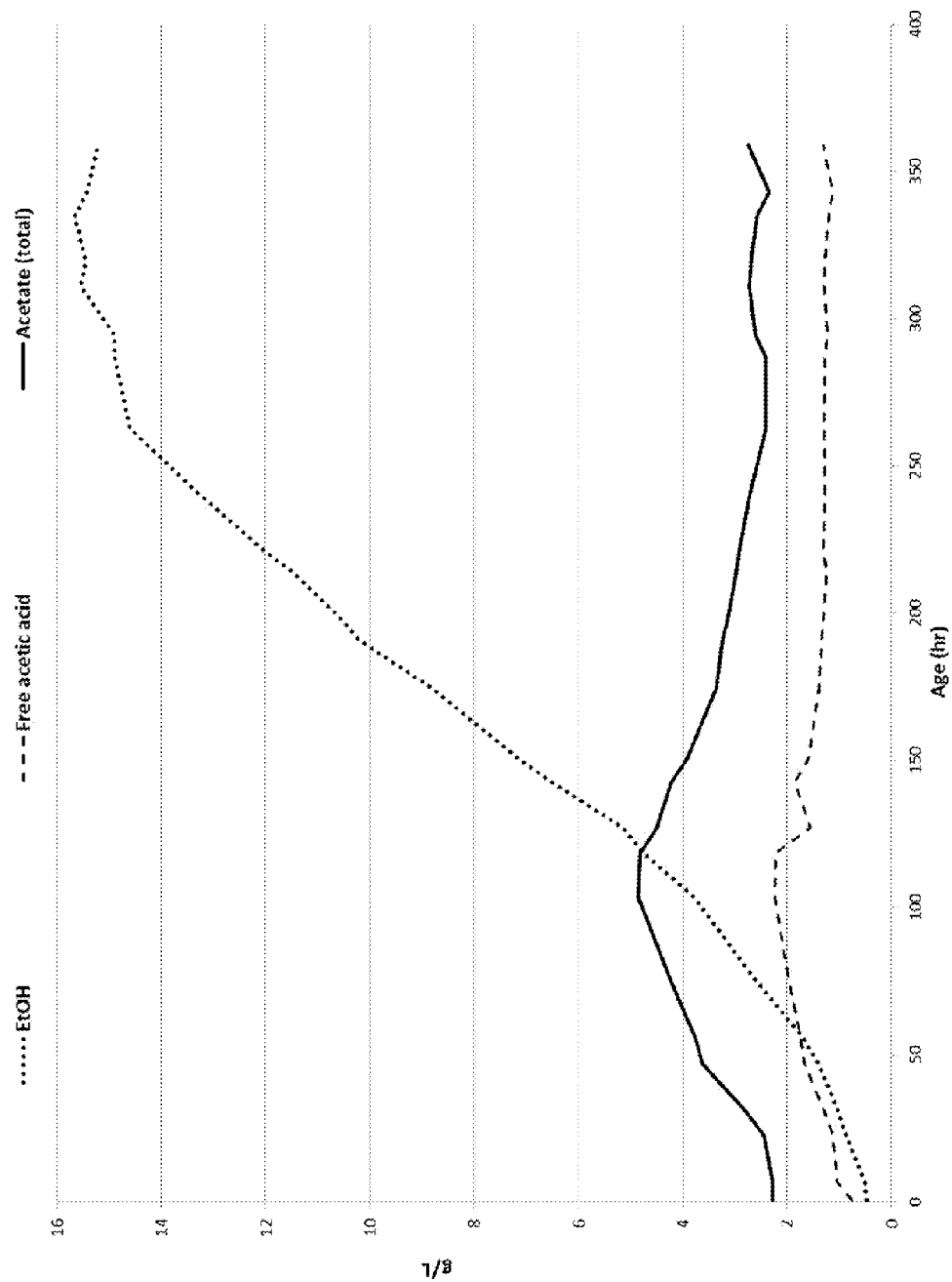

FIG. 19 shows the operational values for the run starting from hour 0 through 360 hours. Agitation was increased rapidly and remained at 377 rpm over the first 20 hours of the run and then increased stepwise to maximum 568 rpm at hour 232 where it remained until hour 288 after which it was decreased to 543 at the end of the run. FIG. 19 shows the fermenter with a steady increase of CO up to about hour 200 at which time the uptake stabilized at high value through the end of the run. Hydrogen uptake tracked a similar increase until about hour 200 after which time it fluctuated at a high level until the end of the run. FIG. 20 shows a plot of the recovery of products for the same run. The results of the product analysis show that the fermentation produced ethanol at a steadily increasing concentration over the course of the run phase up to almost 16 g/L at hour 300. The product data shows an elevated initial level of total acetate that reached its highest level at about 100 hours and then stabilized at below 2.5 g/L through the end of the run. Throughout most of the run phase butanol and butyrate production were below detectable limits of the GC. The depicted phase of the run shows that high concentrations of C2 oxygenates can be obtained with essentially only the addition of bisulfite as the sulfur source to the fermentation and at a pH well below 5.

Example 12

A seed culture comprising *Clostridium coskatii* obtained from the same cryostock as described in Example 1 was grown in a seed vessel and then introduced into the fermentor at the beginning of the continuous fermentation run according to the procedures as previously described. At the initiation of the run (hour 0) the base liquid media entering the fermenter contained no cysteine other than cysteine that was present with the culture as it was transferred from the seed vessel. Bisulfite at a concentration of 0.6 mM was supplied via the media feed over the course of the run to provide 0.5× of a sulfur constituent through hour 120. The concentration of added bisulfite was raised to 0.9 mM to provide a 0.75× concentration at about 120 hours (~0.150 mM/day/OD). Bisulfite was increased to 1.2 mM to provide a 1× concentration of sulfur at hour 224. The chelant used in this experiment was 0.018 g/L sodium citrate. Gas flow was initiated at about 100 mL/min and was gradually increased to 400 mL/min at hour 488 where it remained for the remainder of the run. The gas had an average volumetric composition of 29% CO, 20% $CO_2$, 39% $H_2$ and 11% $CH_4$. Base liquid media addition started at about 1.25 liter per day until hour 26 and was then raised in stages to 1.63 liters per day until hour 95, to 2.5 L/day until hour 120, to 2.83 L/day until hour 153, to 3.31 L/day at hour 177 raised and then to 4 liters per day for the rest of the run. The fermenter operated at ambient pressure until hour 428 when it was raised to 931. Temperature remained at approximately 37° C. The pH, started at 4.9 and was gradually lowered to 4.5 by hour 460 and maintained at that level for the remainder of the run.

Figure 21:
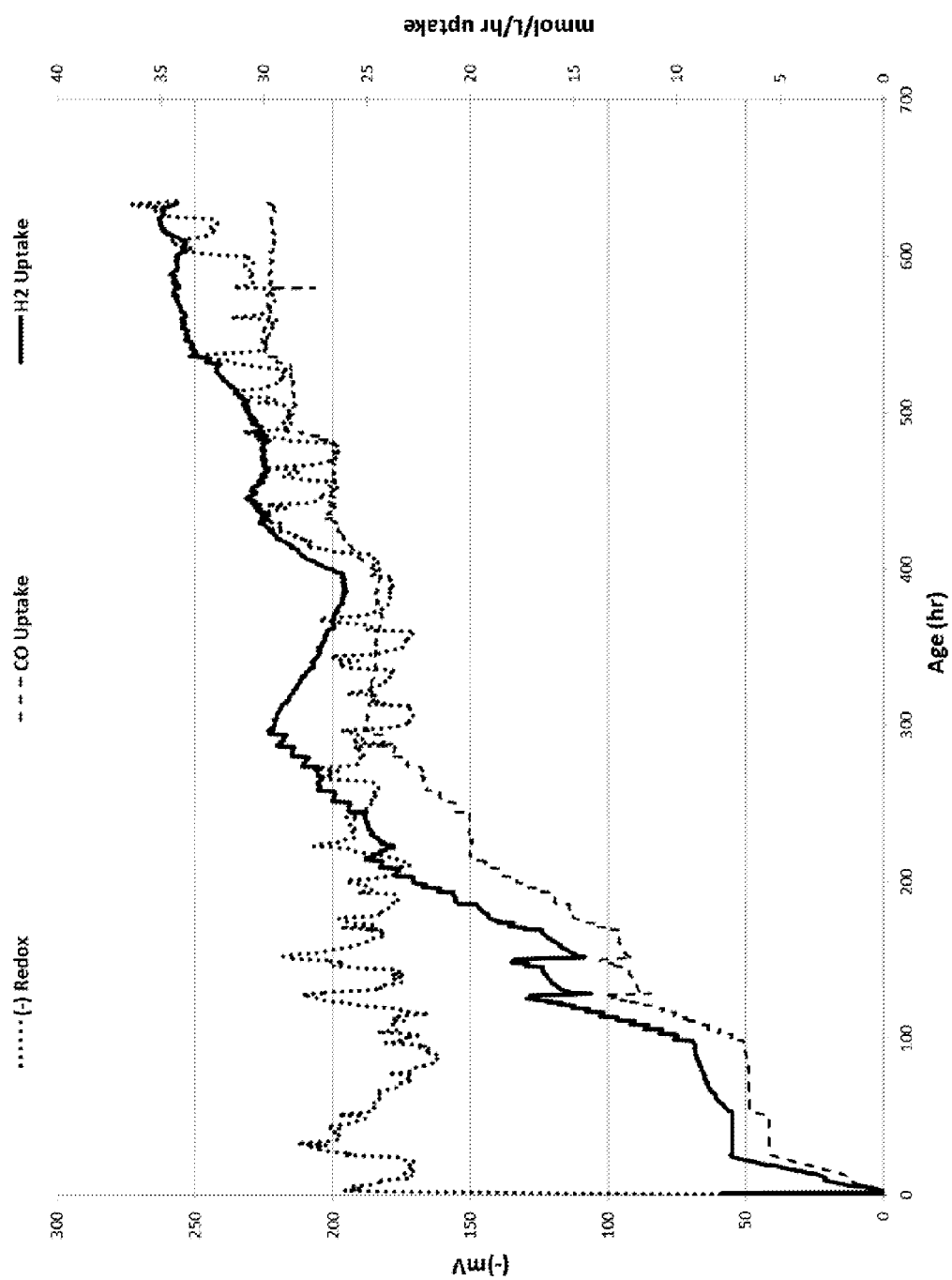

FIG. 21 shows the operational values for the run starting from hour 0 through 360 hours. Agitation began at 355 and was increased gradually to 515 by hour 295 where it stayed for the remainder of the run. FIG. 19 shows the fermenter with a steady increase of CO up to about hour 200 at which time the uptake stabilized at a high value through the end of the run. Hydrogen uptake tracked a similar increase until about hour 200 after which time it fluctuated at a high level until the end of the run.

Figure 22:
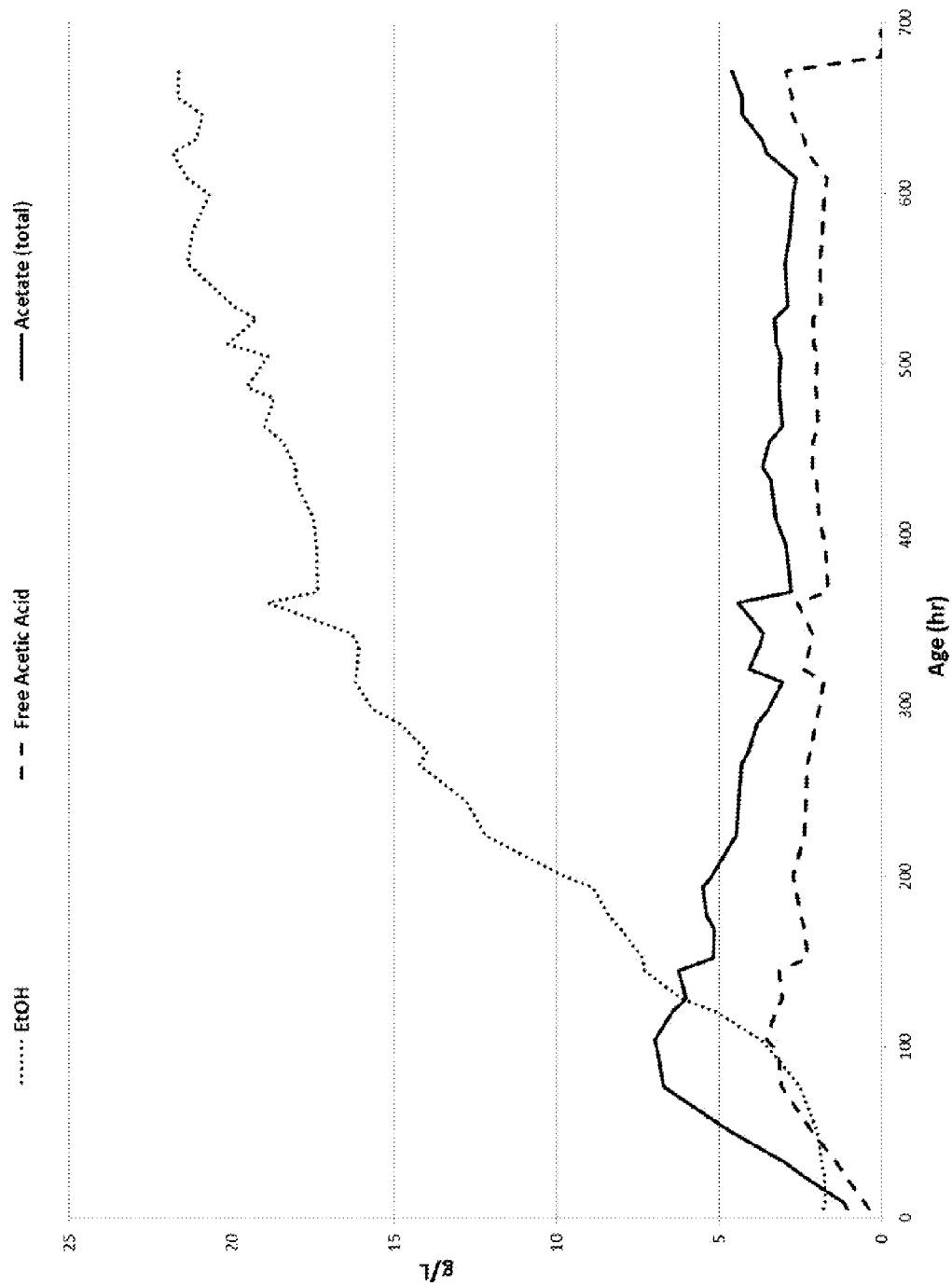

FIG. 22 shows a plot of the recovery of products for the same run. The results of the product analysis show that the fermentation produced ethanol at a steadily increasing concentration over the course of the run phase up to almost 20 g/L at hour 700. The product data shows an elevated initial level of total acetate that reached its highest level at about 100 hours and then stabilized at below 5 g/L through the end of the run. Throughout the most of the run phase butanol and butyrate production were at essentially zero. The depicted phase of the run shows that high concentrations of C2 oxygenates can be obtained with essentially only the addition of bisulfite as the sulfur source to the fermentation and at a pH well below 5.

As described, the present invention provides a number of advantages, some of which have been described above and others which are inherent in the invention. Also, modifications may be proposed without departing from the teachings herein. Accordingly, the scope of the invention is only to be limited as necessitated by the accompanying claims.

It is claimed:

1. A method for producing C2 oxygenates by anaerobic fermentation with an ethanol producing carboxydotrophic microorganism, the method comprising: (a) providing a sulfur additive comprising an S(II) to S(IV) inorganic sulfur compound that produces oxoanions of sulfur in an aqueous fermentation medium, (b) contacting a microbial culture of the microorganism with a substrate comprising carbon monoxide and maintaining the microbial culture in the aqueous fermentation medium containing the sulfur additive and having a pH of less than 5.3, and (c) recovering one or more C2 oxygenates from the aqueous fermentation medium.

2. The method of claim 1 wherein the oxoanions of sulfur include hydrosulfur oxoanions.

3. The method of claim 1 wherein the sulfur additive is an S(III) to S(IV) inorganic sulfur compound that produces oxoanions of sulfur in the aqueous fermentation medium.

4. The method of claim 1 wherein the sulfur additive is selected from the group consisting of sulfurous acid, bisulfite, metabisulfite, dithionite, thiosulfate, and combinations thereof.

5. The method of claim 1 wherein the sulfur additive comprises sodium bisulfite.

6. The method of claim 1 wherein the contacting of step (b) takes place in presence of an organic sulfur source and the concentration of the organic sulfur source is reduced over a predetermined time.

7. The method of claim 6 wherein the concentration of added organic sulfur source in the fermentation medium is less than 0.3 mmol organic sulfur per gram dry cell weight of microorganism.

8. The method of claim 1 wherein the microbial culture is grown in the presence of an organic sulfur source in a first vessel prior to addition of the sulfur additive and step (b) takes place in a second vessel separate from the first vessel.

9. The method of claim 1 wherein the sulfur additive is present in the fermentation medium in a concentration of 0.1 to 10 mmol sulfur per gram dry cell weight of microorganism.

10. The method of claim 1 wherein the sulfur additive is present in the fermentation medium at a concentration between from 0.5 to 2 mmol sulfur per gram dry cell weight of microorganism.

11. The method of claim 1 wherein the fermentation medium is maintained with a cysteine concentration of less than 0.3 mmol per gram dry cell weight of microorganism.

12. The method of claim 1 wherein the pH of the fermentation medium is in a range of 4.3 to 5.1.

13. The method of claim 1 wherein the pH of the fermentation medium is below 4.9.

14. The method of claim 1 wherein the fermentation medium in step (b) contains a chelating agent in a molar ratio range of chelate to total transition metals of from 0.1 to 1.0.

15. The method of claim 14 wherein the chelating agent is selected from the group consisting of ethylenediaminetetraacetic acid, diethylenetriaminepentaaceteic acid, nitrotriacetic acid, sodium citrate, and mixtures thereof.

16. The method of claim 1 wherein the C2 oxygenate comprises ethanol.

17. The method of claim 16 wherein ratio of ethanol to acetate in the fermentation medium of step (c) is such that there are at least five parts of ethanol for every part of acetate.

18. The method of claim 1 wherein the microorganism comprises *Clostridium coskatii, Clostridium ljungdahlii*, or *Clostridium autoethanogenum*.

19. A method for reducing cysteine in the production of ethanol or acetate by anaerobic fermentation comprising:
   a) contacting a microbial culture of a carboxydotrophic microorganism with a substrate comprising carbon monoxide and growing the microbial culture under anaerobic conditions in a first fermentation zone containing cysteine at a first concentration of cysteine to produce a cysteine grown microbial culture in a first fermentation zone;

b) adding the cysteine grown microbial culture to a second fermentation zone containing a sulfur additive comprising an inorganic sulfur compound having a +2 to a +4 oxidation state that produces anions in the second fermentation zone consisting of sulfur atoms combined with oxygen and/or hydrogen atoms and having a lower concentration of cysteine than the first fermentation zone;

c) adding a substrate comprising (i) carbon monoxide, (ii) carbon dioxide and hydrogen, or (iii) mixtures of (i) and (ii) to the second fermentation zone to convert the substrate to C2 oxygenates; and, d) recovering one or more C2 oxygenates from the second fermentation zone.

20. The method of claim 19 wherein the concentration of cysteine in the second fermentation zone is less than 0.3 mmol organic sulfur per gram dry cell weight of microorganism.

21. The method of claim 19 wherein the sulfur additive is selected from the group consisting of sulfurous acid, bisulfite, metabisulfite, and combinations thereof.

22. The method of claim 19 wherein the second fermentation zone has a sulfur additive concentration in a range of 0.5 to 2 mmol sulfur per gram dry cell weight of microorganism.

23. The method of claim 19 wherein a cell culture is withdrawn from the second fermentation zone and transferred to a third fermentation zone that contains the sulfur additive and a reduced concentration of cysteine relative to the second fermentation zone.

24. The method of claim 19 wherein a chelating agent is added to the second fermentation zone.

25. The method of claim 24 wherein the chelating agent is selected from the group consisting of ethylenediaminetetraacetic acid, diethylenetriaminepentaaceteic acid, nitrotriacetic acid, sodium citrate, and mixtures thereof.

26. The method of claim 19 wherein the microorganism comprises *Clostridium coskatii, Clostridium ljungdahlii*, or *Clostridium autoethanogenum*.

27. The method of claim 19 wherein the first fermentation zone has a volume of less than 40,000 liters.

* * * * *